United States Patent
Molenaar et al.

(10) Patent No.: US 10,041,891 B2
(45) Date of Patent: Aug. 7, 2018

(54) SYSTEM FOR RADIOGRAPHIC INSPECTION OF WELDS

(71) Applicant: Rontgen Technische Dienst B.V., Rotterdam (NL)

(72) Inventors: Marcel Meijlom Molenaar, Rotterdam (NL); Martin Ander Hartwigsen, Rotterdam (NL); Bernardus Norbertus Mulder, Rotterdam (NL)

(73) Assignee: RONTGEN TECHNISCHE DIENST B.V., Rotterdam (NL)

( * ) Notice: Subject to any disclaimer, the term of this patent is extended or adjusted under 35 U.S.C. 154(b) by 390 days.

(21) Appl. No.: 14/632,193

(22) Filed: Feb. 26, 2015

(65) Prior Publication Data

US 2015/0241365 A1    Aug. 27, 2015

(30) Foreign Application Priority Data

Feb. 26, 2014    (NL) .................................. 2012329

(51) Int. Cl.
| | |
|---|---|
| *B23K 37/00* | (2006.01) |
| *B23K 37/04* | (2006.01) |
| *G01N 23/18* | (2018.01) |
| *B23K 31/12* | (2006.01) |

(52) U.S. Cl.
CPC ........... *G01N 23/18* (2013.01); *B23K 31/125* (2013.01); *G01N 2223/629* (2013.01); *G01N 2223/631* (2013.01)

(58) Field of Classification Search
CPC .................................................... B23K 31/125
USPC ......................................................... 228/104
See application file for complete search history.

(56) References Cited

U.S. PATENT DOCUMENTS

| | | | | |
|---|---|---|---|---|
| 2,027,302 | A * | 1/1936 | Hacker | ............... B60B 17/0051 |
| | | | | 105/182.1 |
| 3,437,786 | A * | 4/1969 | Colinet | .................. B23K 9/038 |
| | | | | 219/126 |
| 4,490,833 | A | 12/1984 | Inomata et al. | |
| 5,956,077 | A * | 9/1999 | Qureshi | ..................... B25J 9/06 |
| | | | | 348/82 |

(Continued)

FOREIGN PATENT DOCUMENTS

| | | |
|---|---|---|
| DE | 69526170 T2 | 10/2002 |
| FR | 2814240 A1 | 3/2002 |

OTHER PUBLICATIONS

"All Time Automatic Girth Welder" Mar 29, 2011, XP055119312.

*Primary Examiner* — Erin Barry Saad
(74) *Attorney, Agent, or Firm* — Jacobson Holman, PLLC.

(57) ABSTRACT

A system for radiographic inspection of welds from at least a portion of a vertical wall such as the wall of a storage tank for gas or oil wherein the wall comprising a plurality of metal plates connected by means of the welds, the system comprising a frame comprising a first sub frame arranged to be positioned, in use, on a first side of the portion of the wall and a second sub frame arranged to be positioned, in use, on a second side of the portion of the wall which lays opposite to the first side of the portion of the wall. The system comprises a radiation source which is attached to the first sub frame for transmitting electromagnetic radiation towards the weld and a radiation detector which is attached to the second sub frame for detecting radiation which has traveled through the weld for carrying out the inspection.

33 Claims, 13 Drawing Sheets

(56) References Cited

U.S. PATENT DOCUMENTS

| | | |
|---|---|---|
| 6,137,860 A | 10/2000 | Ellegood et al. |
| 2012/0221275 A1* | 8/2012 | Obinata ................. G01N 23/16 |
| | | 702/97 |

* cited by examiner 14.1   14.2   18

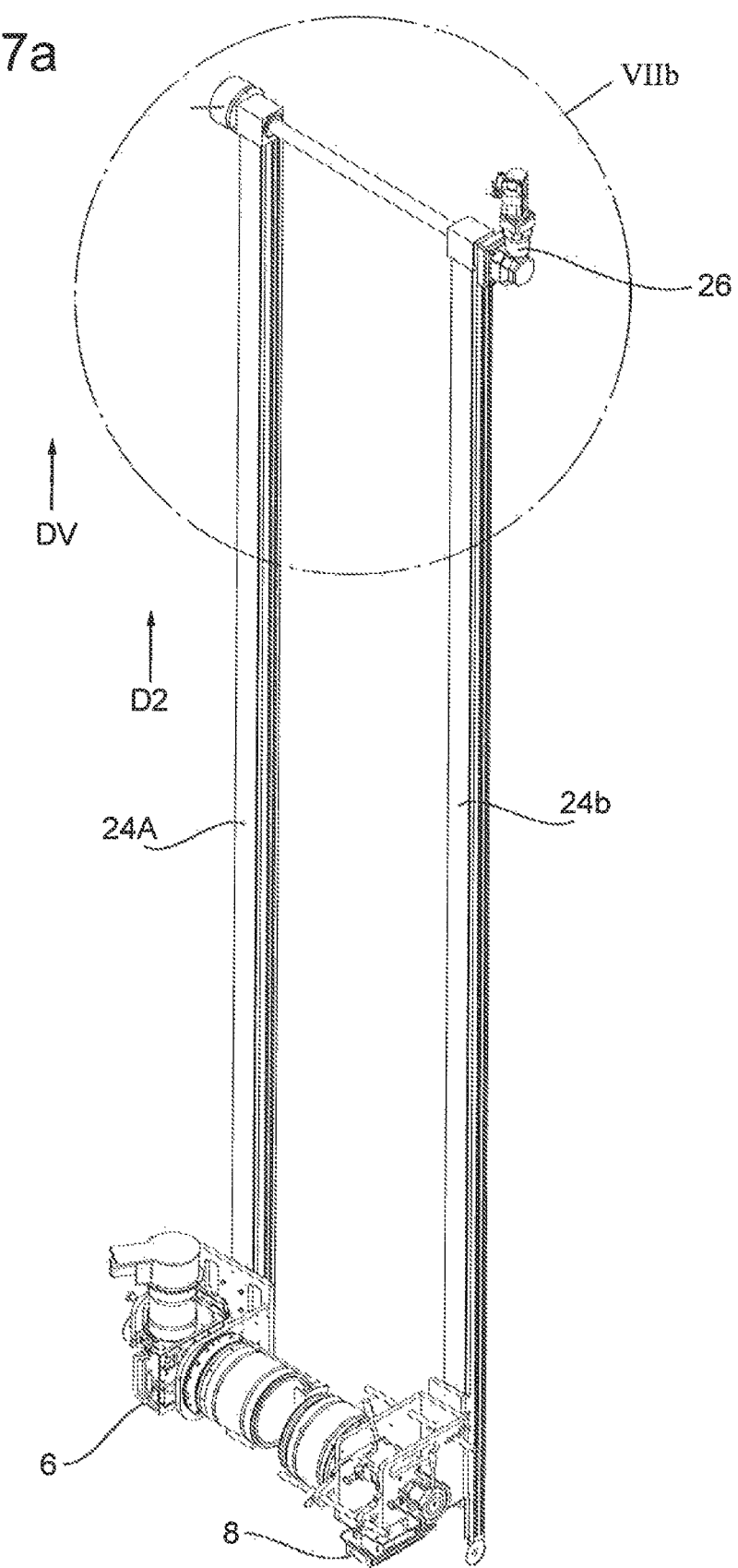

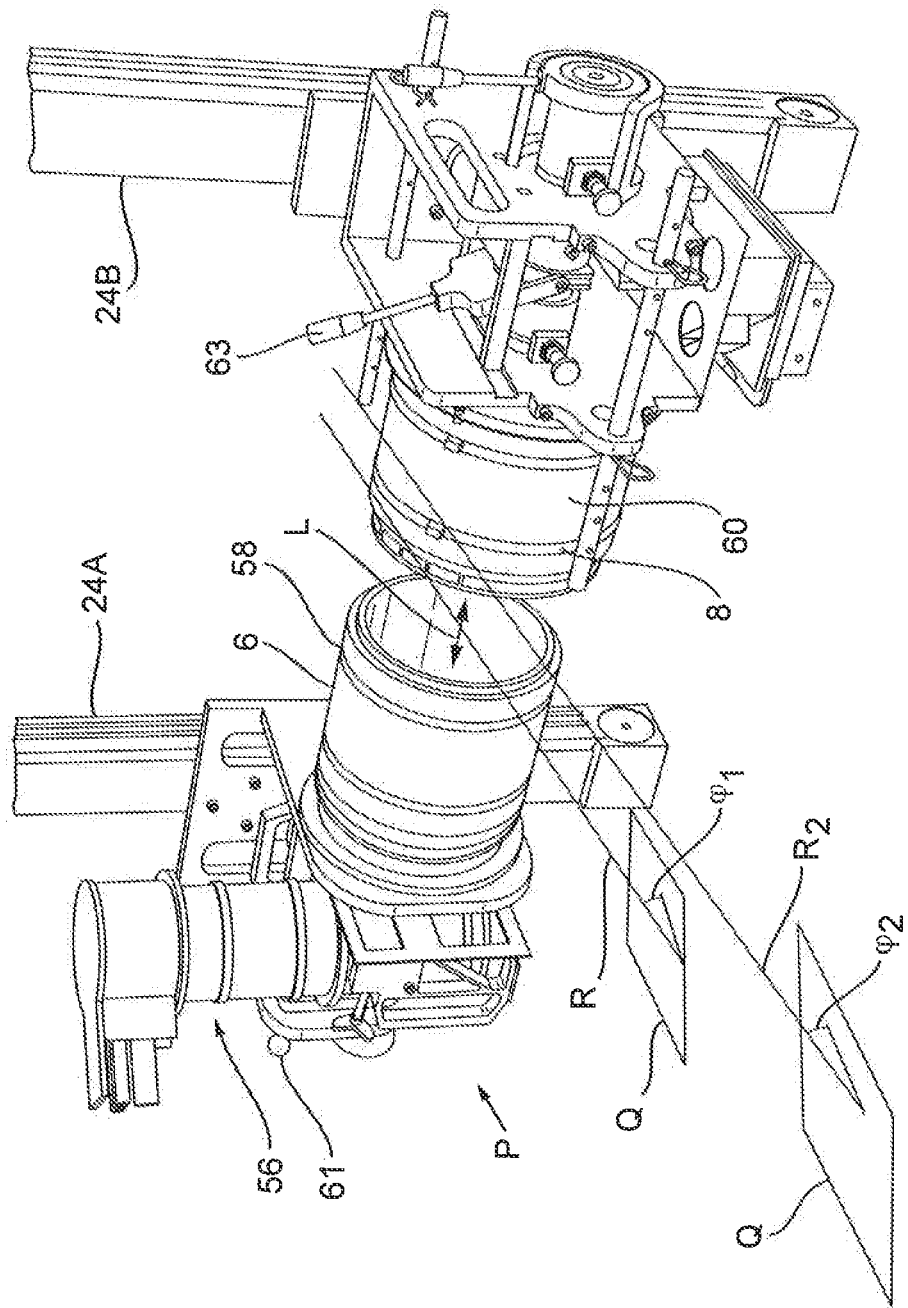

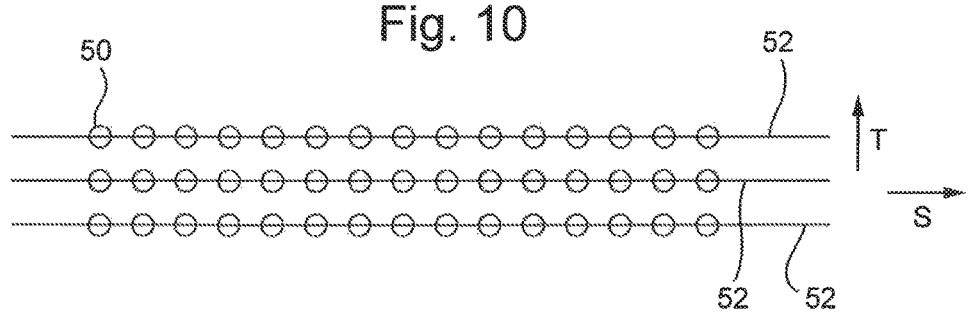
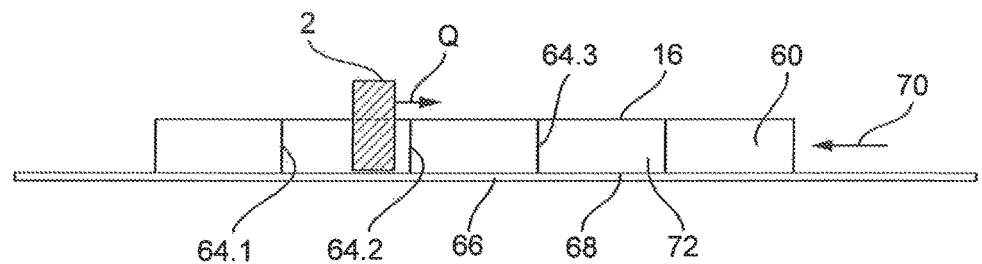
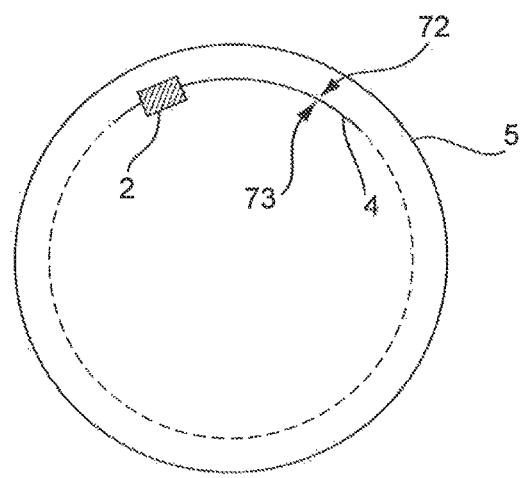

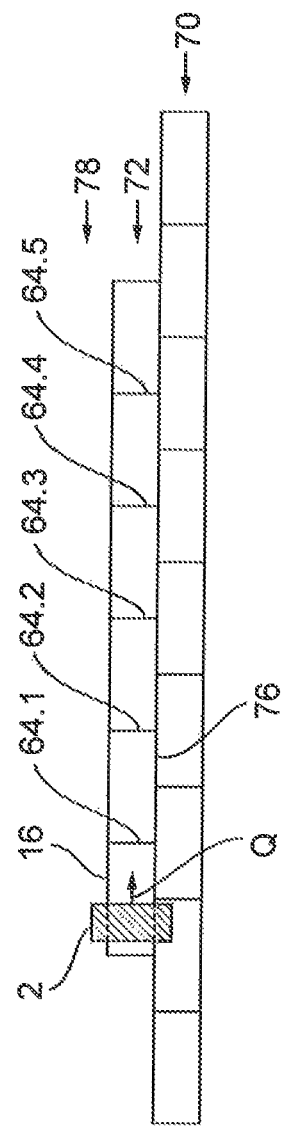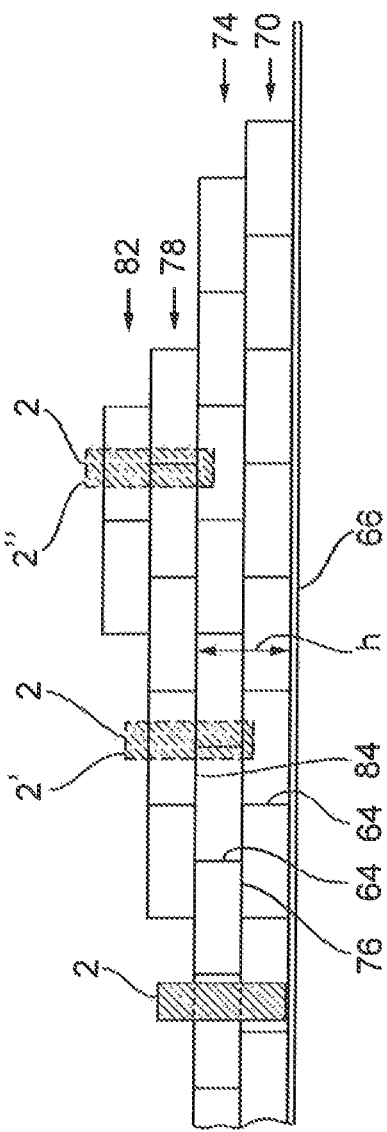

Fig. 14a
Fig. 14b
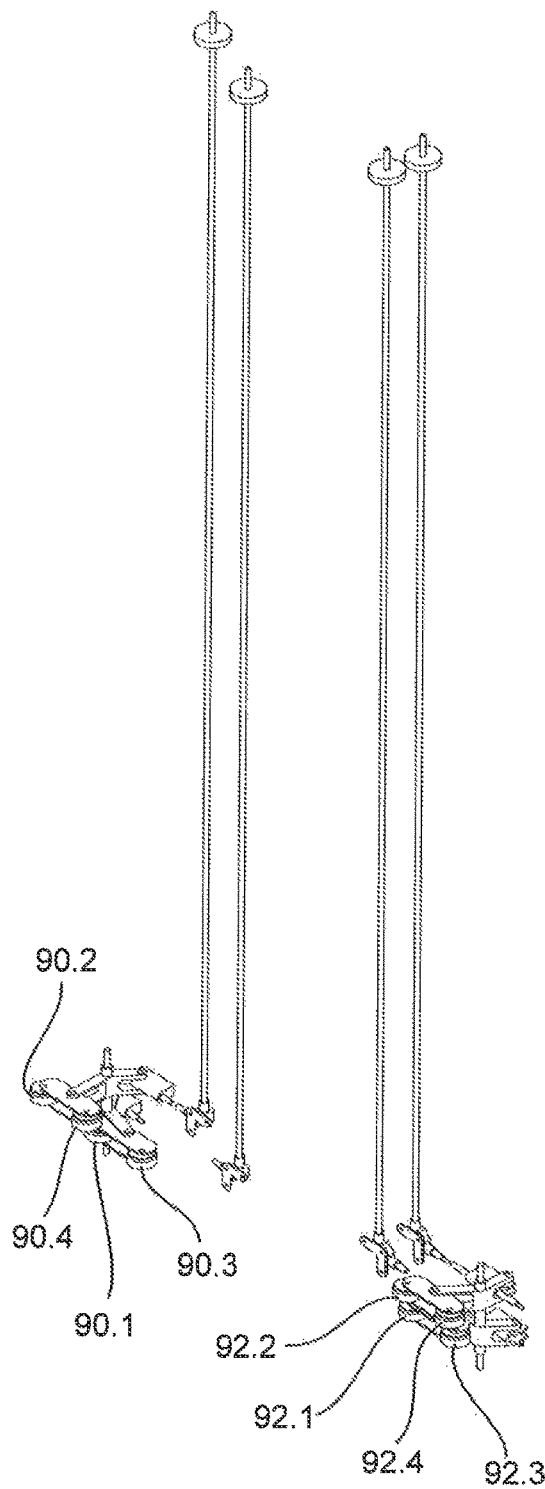
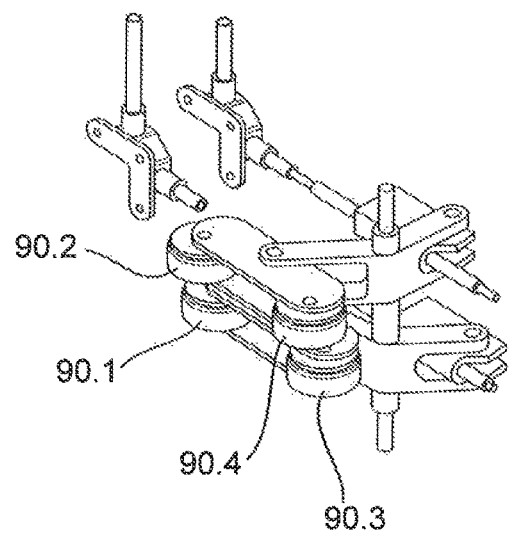

SYSTEM FOR RADIOGRAPHIC INSPECTION OF WELDS

The present invention relates to a system for radiographic inspection of welds from at least a portion of a vertical wall such as the wall of a storage tank for (liquefied) gas or oil wherein the wall comprising a plurality of metal plates connected by means of the welds, the system comprising a frame comprising a first sub frame arranged to be positioned, in use, on a first side of the portion of the wall and a second sub frame arranged to be positioned, in use, on a second side of the portion of the wall which lays opposite to the first side of the portion of the wall wherein the system comprises a radiation source which is attached to the first sub frame for transmitting electromagnetic radiation towards the weld and a radiation detector which is attached to the second sub frame for detecting radiation which has traveled through the weld for carrying out the inspection.

BACKGROUND OF THE INVENTION

Such a system is known from U.S. Pat. No. 4,490,833. The system is used for the examination of welds during construction of a storage tank. These tanks are also referred to as vertical storage tanks as the design basically consists of a vertically positioned cylinder, although the diameter can be up to 100 meters or even larger.

The vertical part of the tank (the shell or wall) is constructed of multiple metal plates. Typically the size of these plates is 10 meters in horizontal direction and 3 meters in vertical direction, but other sizes can be used as well. The thickness of the used plates depends on the design of the tank (diameter, height, plate material etc.) and purpose (pressure, substance to be stored, temperature etc.). Typically the thickness of the vertical plates varies from relatively thick at the bottom to thinner at the top. The lower vertical plates are thicker, for example 25 to 30 mm thickness, to withstand the weight of the plates above and the fluid pressure of the medium stored in the tank. The upper plates can be thinner, for example 10 mm or thinner, because less weight is on top, a lower fluid pressure exists at higher elevation and to limit the amount of required material. Alternatively, all plates of the tank wall could have the same thickness, depending on the design and circumstances.

Depending on the substance to be stored inside the tank the material of the tank plates can be standard low alloy carbon steel (e.g. for crude oil or oil products), or an alloyed steel that is suitable for the stored product or circumstances (e.g. 9% Ni steel for storage of LNG, Liquefied Natural Gas, at −162° C.). Some storage tanks are made of non ferritic material like aluminium.

Typically all welds (horizontal and vertical) between the plates of the tank shell (wall) must be examined to ensure the integrity of the welds.

Some welds are more difficult to access or to examine, for example the weld connecting the tank wall and the (horizontal) bottom plates of the tank floor. These welds and the welds between the plates of the tank bottom plates are not considered here. The welds to be inspected are the welds between the metal plates.

A disadvantage of the known system is that films are used allowing only one exposure a time. This is slow and requires chemical processing of the film.

Digital radiography is also known as such and covers a variety of technologies, comparable to the medical sector, like:

Image plates that have a layer sensitive to X-rays (like a phosphor plate) that temporary stores a latent image. The latent image can be read by a dedicated scanner device and then the image is stored on a computer;

Flat panel, utilising a material that converts the X-rays into digital signals (directly or indirectly), for example an amorphous silicon panel, connected to a computer on which the digital signals are stored as image.

The above technologies are only suitable for static exposure, meaning that both the X-ray source and the detector (film, image plate, or flat panel) have to be stationary relative to each other and to the object during the exposure of the detector to radiation. The maximum size of a film, image plate or flat panel is typically about 30 to 40 centimeters which determines the maximum weld length that can be examined in one exposure. To ensure that the entire length of the weld is examined it is required that consecutive exposures overlap, for example 5 centimeters, so the effective exposed length is always shorter than the size of the film or detector. As a result much time is involved in handling and positioning of the equipment to a next stationary position for making a new exposure. As explained for films and image plates also additional processing (development, read-out) is required.

Conventional radiography with films uses static exposures and requires operator handling on both sides of the tank wall (for the X-ray source and for the films), for exposure of each individual film.

Systems for digital radiography mainly use static exposures, for example on flat panel detectors. Therefore operator handling would be required on both sides of the tank wall, similar to conventional radiography.

For radiographic weld examination strict requirements apply to the image quality of the resulting image to ensure proper detection and evaluation of possible welding imperfections. These requirements are available in (inter)national codes and standards and are, for example, resolution and contrast. To show that the system meets the requirements it is mandatory that image quality indicators are attached to the weld and are visible on the resulting image, according to the codes and standards. For digital systems additional requirements can apply. Not all available digital systems are able to fulfil the requirements for weld examination of storage tanks.

Due to radiation safety regulations no other personnel is allowed during radiographic examination, a so called exclusion zone must be established. Depending on the situation the exclusion zone can extend over part or even the complete tank. Obviously, this limits the construction progress (welding etc.). Typically the welding and construction activities are performed during the day shift while the radiographic examination is performed during the night shift. It could be beneficial to have multiple construction/welding shifts working consecutively around the clock (24 hours per day) but this interferes with the radiographic examination due to radiation safety. In many construction projects the examination of welds is on the critical path of the construction process, so the progress of the whole project depends directly on the progress of the examinations.

Some welding imperfections can be related to the welding process, welding materials and settings of the welding system. For example the speed at which the welder, or the welding machine, proceeds during welding can influence the weld quality. It is important that information about the weld quality is provided to the welder as soon as possible, to enable the welder to adjust any parameter of the welding process if required. Such feedback on weld quality can consist of, for example, the presence of small imperfections which are not of direct relevance for the quality of that weld but still indicate a sub-optimal setting of the welding parameters. If the welding parameters are not adjusted then possibly in the next welds larger imperfections could occur which are not allowed and the weld has to be repaired, possibly over larger distances. Such repairs require additional work (removing part of the weld, re-welding and re-examination) which could ultimately interfere with the scheduled construction progress. So, if the feedback on weld quality is provided earlier to the welder it may be possible to adjust the welding parameters timely and prevent the occurrence of larger, not allowable imperfections. The early feedback to the welder is only possible if the progress of the examination of the welds can keep up with the welding progress and the examination can be performed as close as possible to the welding.

BRIEF SUMMARY OF THE INVENTION

The object of the invention is to solve at least some and preferably each of the above referred to problems.

The system according to the invention is characterised in that the system is arranged such that in use, the first sub frame and the second sub frame are mechanically and rigidly connected to each other wherein the system is further provided with suspension transportation means such as suspension wheels connected to the frame, preferably to an upper portion of the frame or an upper half portion of the frame wherein the suspension transportation means are arranged, in use, to be positioned on an upper free edge of the portion of the wall so that the frame can drive over the upper free edge of the portion of the wall for scanning a weld to be inspected by means of the radiation source and the radiation detector wherein the weld extends in a direction of the upper edge of the portion of the wall.

Thus according to the invention an inspection of the weld extending in the direction of the upper edge can be carried out while moving and by moving the system over the upper edge of the portion of the wall. This implies that a scan is carried out in stead of a series of exposures wherein the frame is stationary during each exposure.

So far, only convention film radiography and flat panel digital radiographic systems are used for the examination of welds in tank walls, with static exposures. No dynamic/scanning systems are available yet.

The distances, especially between the tank plate and the detector, must preferably be accurately constant. For example, if a straight guide rail is used to examine a horizontal weld then the distance between the detector and the tank wall will vary due to the curvature (diameter) of the tank. This has a large impact on image quality, which makes this approach not suitable. In addition the alignment between source and detector is difficult to maintain. However the system while scanning in the direction of the upper edge will automatically follow a curvature of the portion of the wall. In addition, for dynamic exposure also stability (no vibration, no shocks, fixed distances) are important. Also a proper alignment between source and detector will be maintained during scanning because the frame is moved as a whole during scanning in the direction of the upper edge.

Because in accordance with the invention the first sub frame and the second sub frame are rigidly connected to each other, the whole frame is rigid and the system can be stable and used for dynamic scanning with a lowered risk that during scanning the radiation source and the radiation detector are vibrating. Here, rigidly connected covers at least the directions parallel to the plates. Optionally, some limited movement perpendicular to the plates is possible for the lower ends of the frames, where the support wheels are located. Preferably the frame has the shape of an inverted U. This provides a stable character to the system once it is suspended on the upper edge of the portion of the wall. Preferably it holds that the first sub frame has a longitudinal shape extending in a vertical direction and/or wherein the second sub frame has a longitudinal shape extending in a vertical direction.

In accordance with a preferred embodiment it further holds that the system is provided with at least a first motor for driving the suspension transportation means such as the suspension wheels or other wheels which, in use are in contact with an outer surface of the portion of the wall for scanning a weld which extends along the direction of the upper edge of the portion of the wall.

Also a steady state of scanning speed can be realized by means of the first motor. Thus it holds that in accordance with the preferred embodiment the system is arranged, in use, to perform the scanning in the direction of the upper edge by moving the complete system at a substantially constant speed.

In accordance with the practical embodiment it holds that the radiation source and the radiation detector are aligned to each other, such that radiation which is transmitted by the radiation source could directly travel to the radiation detector along a straight line if there would not be present a portion of the wall between the radiation source and the radiation detector.

In accordance to a special embodiment it holds that the system comprises a plurality of suspension wheels which are separated from each other in a horizontal direction.

In that case it preferably holds that the radiation source and the radiation detector lay in a vertical plane wherein at least one of the suspension wheels lays on a first side of the vertical plane an at least another of the suspension wheels lays on an other side of the vertical plane. Also this special embodiment provides an additional stability to the frame in use while scanning in the direction of the upper axis of the portion of the wall.

In accordance with a special embodiment it holds that the radiation source is movably in a second direction comprising a vertical component, attached to the first sub frame wherein the radiation detector is movably in the second direction attached to the second sub frame and wherein the system is provided with a second motor for moving the radiation source and radiation detector synchronously in the second direction for scanning a weld which extend in the second direction.

Thus, in that case the system is also designed for scanning welds in the second direction wherein in a practical embodiment the second direction is a vertical direction. This in view of the fact that the plates are generally welded to each other by means of welds which extend in the direction of the upper portion of the wall, usually a horizontal direction, and welds which extend in the vertical direction. Preferably it holds that the radiation source and the radiation detector are moved by means of a spindle or toothed belt driven by the second motor. Because the radiation source and radiation detector are moved by one and the same second motor the radiation source and radiation detector will move synchronously relative to each other.

According to a practical embodiment it holds that the system is arranged to perform, in use, a scan in the second direction while the suspension means, in particular the suspension wheels are stationary. Thus according to a practical embodiment it holds that the system is arranged to perform, in use, a scan in the second direction while the frame is kept stationary In this way the welds which extend in the second direction, practically in the vertical direction, can be scanned in a very precise manner. Also in this case the alignment between the detector and the source is maintained wherein vibrations can be limited because the frame as a whole is kept stationary.

Preferably it holds that the system is provided with a damped suspension between the suspensions means such as the suspension wheels and the frame. In this embodiment additional measures are taken for demping vibrations of the radiation source and radiation detector while scanning in the direction of the upper edge.

In order to further stabilize the frame during scanning, it may hold that the first sub frame is provided with at least one first support wheel wherein a rotational axis of the first support wheels extends in a vertical direction and wherein the first support wheel is arranged to roll along a surface of the portion of the wall if the system is moved over the upper edge and/or wherein the second sub frame is provided with at least one second support wheel wherein a rotational axis of the second support wheels extends in a vertical direction and wherein the second support wheel is arranged to roll along a surface of the portion of the wall if the system is driven over the upper edge.

Preferably in that case the first sub frame is provided with at least two first support wheels which are separated in at least a vertical direction from each other and wherein a rotational axis of the first support wheels extends in a vertical direction and wherein the first support wheels are arranged to roll along a surface of the portion of the wall if the system is moved over the upper edge and/or wherein the second sub frame is provided with at least two second support wheels which are separated in at least a vertical direction from each other and wherein a rotational axis of the second support wheels extends in a vertical direction and wherein the second support wheels are arranged to roll along a surface of the portion of the wall if the system is driven over the upper edge.

It preferably holds that the contact force between a support wheel and a surface of the wall can be optimized for providing an optimal stability to the frame while scanning.

In accordance with a preferred embodiment it holds that the radiation source is a line radiation source and/or in that the radiation detector is a line radiation detector. For clarity it should be noted that 'line radiation source' within the context of this application actually refers to the shape of the radiation beam generated by the radiation source, not the shape of the source itself. Often the radiation source itself is basically a point source while the beam is shaped by a tungsten collimator. So the radiation beam projected on the detector has the shape of a line, or substantially a line. For clarity it should also be noted that in this application line detector means a detector that is substantially in the shape of a line, with a main direction that is significantly larger compared to a perpendicular direction. Although it consists of multiple lines (which are each sensitive for detecting radiation and may each comprise a plurality of pixels for example in case the detector is a digital detector) the length of the lines is substantially longer than the distance across the lines. In that case in accordance with an preferred embodiment it holds that the system is arranged to adjust an orientation of the radiation source for adjusting a angle between the line of the radiation source and a horizontal plane and/or in that the system is arranged to adjust an orientation of the radiation detector for adjusting an angle between the line of the radiation detector and a horizontal plane. In this way one and the same line radiation source and the same line detector can be used both for scanning welds which extend in the direction of the edge and welds which extend in the second direction. In that case the longitudinal direction of a line detector as well as a longitudinal direction of the line source will be directed perpendicular to a weld to be scanned.

Preferably it holds that the radiation detector is a digital detector wherein for example the data generated by means of the detector during the examination is transferred to a computer positioned on the tank floor for later evaluation. In this way the detected radiation can be analysed immediately by means of a computer. Therefore it preferably holds that the system is provided with a computer connected to the digital connector for preferably instantaneously creating an image of the scanned weld on a screen.

In accordance with a practical embodiment it holds that the radiation source is an X-ray radiation source. In that case it preferably holds that the system is provided with a first radiation shield for shielding the radiation source, preferably in all directions accept for a direction from the radiation source towards the radiation detector.

It also preferably holds that the system is provided with a second radiation shield for shielding the radiation detector, preferably in all directions accept for a direction from the radiation source towards the radiation detector.

In this way workers for example workers who are welding new plates to the wall under construction can work during scanning of previously applied welds. Thus the inspection can be carried out at the same time as that new plates are welded to the wall under construction. In that case the workers only have to take care of providing a predetermined minimum distance between the radiation source, the radiation detector on the one hand and the worker on the other hand. Preferably it holds further that the system is provided with a third radiation shield which surrounds a path along which the radiation travels, in use from the radiation source to portion of the wall and/or from the portion of the wall towards the radiation detector.

The invention also relates to a method for constructing a vertical wall and scanning welds of the vertical wall wherein such method is carried out by means of the system according to the present invention. The method comprises the following steps:

1. Constructing at least a portion of a first lowest ring of the wall by welding metal plates to each other wherein the finished lowest ring comprises a plurality of metal plates which are connected to each other by vertically extending welds and possibly horizontally extending weld;

2. Installing the system so that the suspension means are positioned on an upper edge of the portion of the first ring of the tank wall which has been constructed in step 1;

3. Carrying out inspection of a vertical weld by moving the radiation source and the radiation detector synchronously in a vertical direction while keeping the frame stationary relative to the upper edge of the portion of the first ring;

4. Moving the system along the upper edge of the portion of the first ring to another position and repeat step 3.

5. Repeating step 4 until all vertical welds of the portion of the first ring have been scanned;

6. Optionally inspecting a horizontal weld between plates of the first ring by moving the system over the upper edge of the first ring;

7. Repeating step 1-6 until the first ring is fully constructed and each weld of the first ring is inspected;

8. At least partly removing the system from the first ring of the tank wall and possibly adjusting the vertical position of the suspension wheels on the system;

9. Constructing at least a portion of a next ring on top of the last ring inspected wherein the plates of the next ring are connected to each other by vertical welds and optionally horizontal welds and wherein plates of the next ring are attached to plates of the last ring by means of a horizontal weld;

10. Installing the system so that the suspension means are positioned on an upper edge of at least a portion of the next ring of the tank wall which has been constructed in step 9;

11. Carry out inspection of a vertical weld by moving the radiation source and the radiation detector synchronously in a vertical direction while keeping the frame stationary relative to the upper edge of the next ring;

12. Moving the system along the upper edge of the next ring to another position and repeat step 11.

13. Repeating step 12 until all vertical welds of the portion of the next ring have been scanned;

14. Moving the frame over the upper edge of the portion of the next ring for scanning the weld between the portion of the next ring and a last ring manufactured below the next ring and optionally for scanning the horizontal weld between the plates of the next ring;

15. Repeat steps 9-14 until the next ring is complete constructed and each vertical weld of the next ring is inspected, the complete horizontal weld between the next ring and the last ring as mentioned in step 9 also inspected and optionally the at least one horizontal weld between the plates of the next ring are inspected;

16. At least partly removing the system from the next ring of the tank wall;

17. Repeating steps 9-16 until the wall of the tank is finished and preferably each weld has been inspected. It will be clear that the numbering of the method steps does not necessarily imply an order of the method steps. For example the order of the steps 11-14 can be varied and is not fixed, and can be for example 11, 12, 13, 14 or 14, 11, 12, 13

The new scanner system is thus designed to meet some or all of the following requirements, to overcome the limitations of existing systems/approaches:

Capable to perform dynamic examination (scanning), meaning that the system moves at a certain speed while the weld is examined (no static exposures);

Can easily switch between horizontal and vertical welds (two scanning directions);

Maintain alignment between the radiation source and the radiation detector during dynamic examination (scanning), both in horizontal and vertical direction;
  The alignments be stable (robust, no vibrations) to avoid influences on the required image quality. This is achieved by mechanically linking the radiation source and the radiation detector using a stiff frame. The vertical alignment can be done mechanically;

Can perform the examination at a speed that is suitable to keep up with welding progress (so the examination is no longer at the critical path of the construction process);
  Note that the overall examination speed includes the time required for scanning a weld (scanning speed, for example 10 or 15 millimeter/second), but also the time required for handling the whole scanner system like moving to another weld, positioning etc. Basically, the overall examination speed is the amount of weld length (meters) that can be examined on one day or in one working shift;

Has all functions inside the frame (robust, safe for handling and lifting, short cables for high voltage to the radiation source);

No influence of wall curvature due to the tank diameter;
  Design is suitable for a wide range of tank diameters, during horizontal movement the scanner follows the round contour of the tank wall;
  The detector is at a fixed distance to the tank wall (using support wheels);

Shields the radiation, safe working distance is 3 meters from the contours of the scanner frame;

Remote controlled (outside the frame;

Carries all required equipment, no more heavy labour for the operators (radiation source, detector, power supplies, etc).

BRIEF DESCRIPTION OF THE SEVERAL VIEWS OF THE DRAWINGS

A possible embodiment of the invention will now be discussed based on the drawings wherein:

FIG. 7a shows two vertical guiderails provided with a second motor incorporated in the frame of the system as shown in FIG. 1;

FIG. 7b shows a detail of FIG. 7a;

FIG. 7c shows a detail of FIG. 7a;

FIG. 10 shows schematically a possible the arrangement of the pixels of a digital radiation detector;

FIG. 11a shows the construction of a lower first ring of plates from a wall;

FIG. 11b shows a top view of the wall of FIG. 11a;

FIG. 12 shows the construction of FIG. 11a wherein a portion of a next ring is attached to the lower ring.

FIG. 13 shows the partial construction of a wall as shown in FIG. 11a wherein the plates have a height which is smaller than the plates as shown in FIG. 11a;

FIG. 14a shows a detail of FIG. 3;

FIG. 14b shows a detail of FIG. 14a.

DETAILED DESCRIPTION OF THE INVENTION

Figure 1:
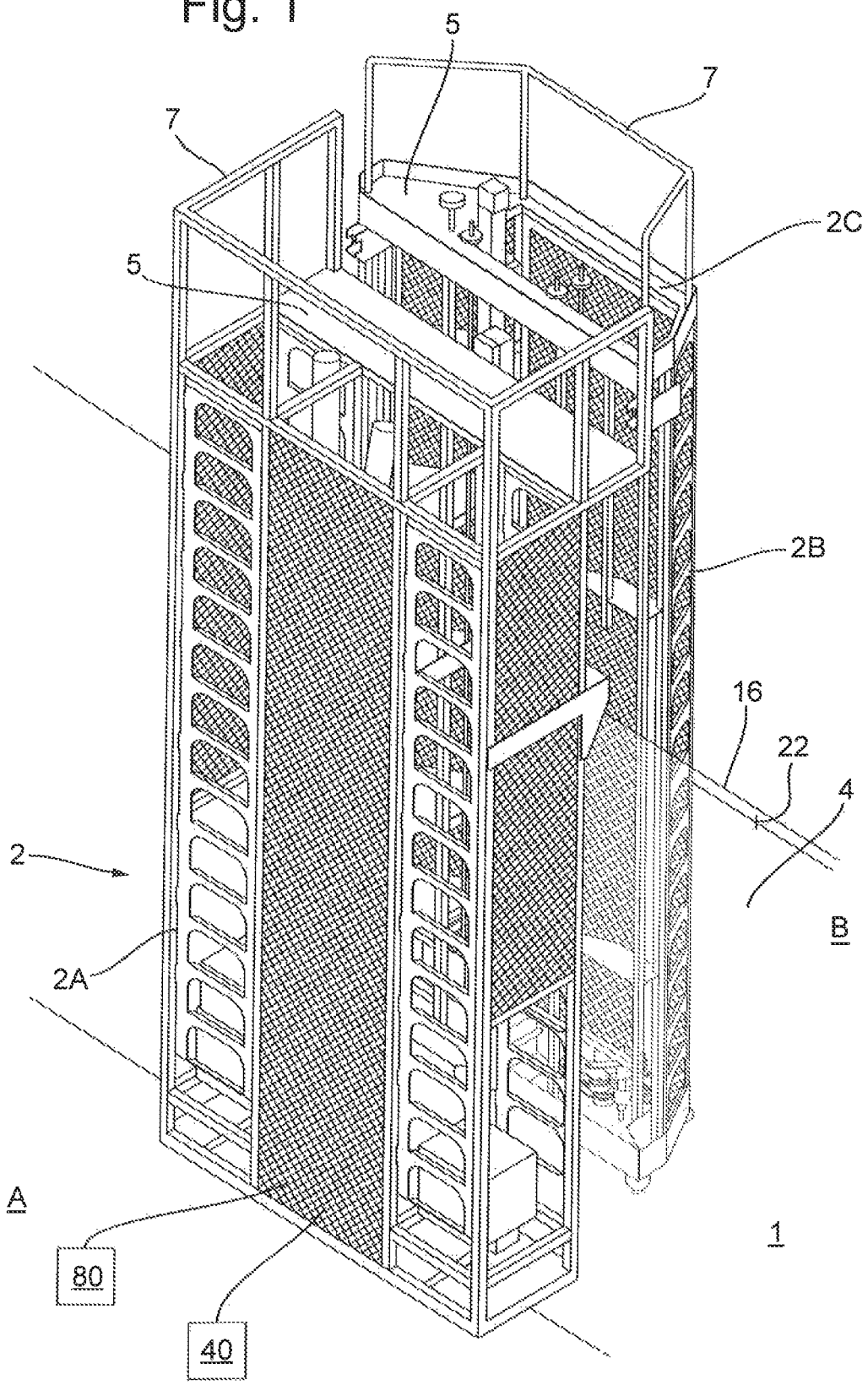
FIG. 1 shows an overview of a system of a possible embodiment of the system according to the invention on a vertical wall.

In FIG. 1 reference number. 1 indicates a system for radiographic inspection of at least a portion of a vertical wall such as the wall of a storage tank for gas or oil. The system 1 comprises a frame 2 which comprises a first sub frame 2A arranged to be positioned in use, on a first side A of a portion of the wall 4. The frame 2 further comprises a second sub frame 2B arranged to be, in use, on a second side B of the portion of the wall 4, which lays opposite to the first side A of the portion of the wall 4. Each of the sub frames 2A, 2B extends downwardly from a top portion 2C of the frame 2. In this example the top portion 2C is formed by the floors 5 on top of the first sub frame and the second sub frame respectively and which are each at least partially surrounded by a fence 7. The system further comprises a radiation source 6 which is attached to the first sub frame 2A for transmitting electromagnetic radiation towards a weld of the wall 4. Furthermore the system comprises a radiation detector 8 which is attached to the second sub frame 2B for detecting radiation which has traveled through the weld of the at least one portion of the wall 4 for carrying out the inspection. The system is arranged so that, in use, the first sub frame and the second sub frame are mechanically and rigidly connected to each other. In this specific embodiment the top portion 2C and the first sub frame 2A are rigidly integrated to each other as a whole. The second sub frame 2B is provided with hooks 10 for directly connecting the second sub frame 2B to the first sub frame 2A in a rigid manner. In this way the first sub frame 2A and the second sub frame 2B are rigidly connected to each other wherein the frame as a whole is rigid, at least in the plane of the vertical plates. The reason that the sub frame 2B can be disconnected from the first sub frame 2A has to do with installation of the system on a wall and subsequent removal as will be explained hereinafter.

As can be seen from FIG. 1 the frame has a shape of an inverted U. The first sub frame 2A has a longitudinal shape extending in a vertical direction. Also the second sub frame 2B has a longitudinal shape extending in a vertical direction. The first sub frame and the second sub frame are arranged to be connected to each other for using the system and lifting the complete frame from the wall and possibly positioning the system on another portion of the wall. The first sub frame and the second sub frame are arranged to be disconnected from each other for removing the system from the wall, especially when the construction of the wall is finalised and/or if due to a lack of free space the frame can not be lifted form the wall as a whole . . . .

Figure 4:
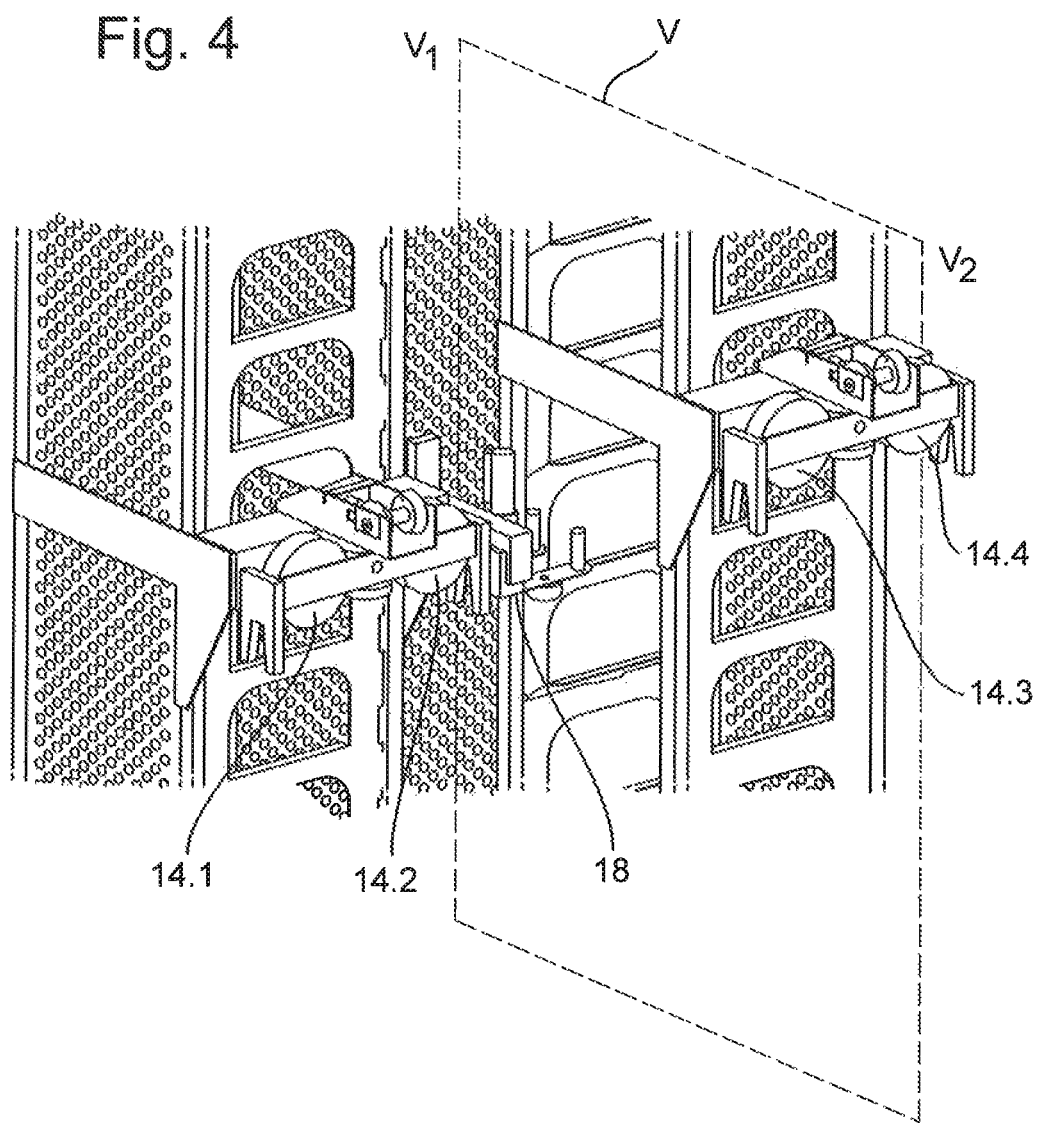
FIG. 4 shows an embodiment of the suspension means provided on the first sub frame as shown in FIG. 2.

The system is further provided with suspension transportation means 12. In this example the transportation means 12 are attached to the first sub frame 2A as can be shown in FIG. 2. More details are shown in FIG. 4. The suspension transportation means comprise four suspension wheels 14.1-14.4 which are arranged to be positioned on an upper edge 16 of a portion of the wall which has been constructed as shown in FIG. 1. In this example the wheels 14.1-14.4 of the suspension transportation means are connected to an upper portion of the frame, more specifically in this example to an upper portion of the first sub frame and to an upper half portion if the first sub frame. The wheels 14.1-14.4 are mounted to the first sub frame in such a way that the location where the wheels are mounted to the first sub frame can be adjusted in a vertical direction depending on the height of the plates of the wall to be inspected. The wheels are intended to be positioned on the upper edge of the portion of the wall so that the frame can drive over the upper edge 16 of the wall for scanning a weld to be inspected by means of the radiation source and the radiation detector. These welds extend in a direction of the upper edge of the portion of the wall. In this example the frame is further provided with a movement means 18, 19, in this example a drive wheel 18 wherein the drive wheel 18 is arranged adjacent the suspension wheels 14.1 and 14.2. The drive wheel 18 is shown in more detail in FIG. 6. The drive wheel 18 is driven by a motor 20 In use the drive wheel 18 is in contact with an outer surface of the wall, a portion of which outer surface is indicated with Ref. No. 22 as shown in FIG. 1. Thus, the outer surface area, which is in contact with the driving wheel 18, lays in this example just below the upper free edge 16 of the wall 4. On the opposite side of plate 4 the system is further provided with a wheel 19 positioned in contact with the surface of the plate. By mechanically clamping the drive wheel 18 and the wheel 19 together the pressure on drive wheel 18 is sufficient to avoid slip on the surface 22. It is noted that in this example the driving wheel 18 is positioned close to the suspension wheels 14.1 to 14.2. It is however possible that the driving wheel is positioned for example on a lower half portion of the first sub frame. Thus in that case the suspension transmission means comprise suspension wheels which are located in the upper half of the first sub frame wherein the driving wheel is located in the lower half of the first sub frame. It is however also possible that the suspension wheels 14.1-14.4 are driving wheels at the same time so that the driving wheel 18 can be omitted. In that case the suspension transportation means also comprise the movement means. It is also possible that the suspension wheels 14.1 to 14.4 are driven by one and the same motor. It is however possible that the driving wheel is positioned on the second sub frame.

Thus the system is arranged to perform the scanning in the direction of the upper edge by moving the complete system at a substantially constant speed by activating the motor 20.

As is shown in FIG. 4 the system comprises a plurality of suspension wheels which are separated from each other in a horizontal direction. In this embodiment it further holds that the radiation source and the radiation detector lay in a vertical plane V wherein at least one of the suspension wheels lays on the first side V1 of the vertical plane (in this case the suspension wheels 14.1 and 14.2) and wherein at least another of the suspension wheels (in this case suspension wheels 14.3 and 14.4) lay on another side V2 of the vertical plane V. This again provides additional stability to the source 6 and the detector.

The radiation source 6 and the radiation detector 8 are aligned to each other such that the radiation which is transmitted by the radiation source could directly travel to the radiation detector along a straight line L as shown in FIG. 7C if there would not be a portion of the wall present between the radiation source and the radiation detector.

Figure 7B:
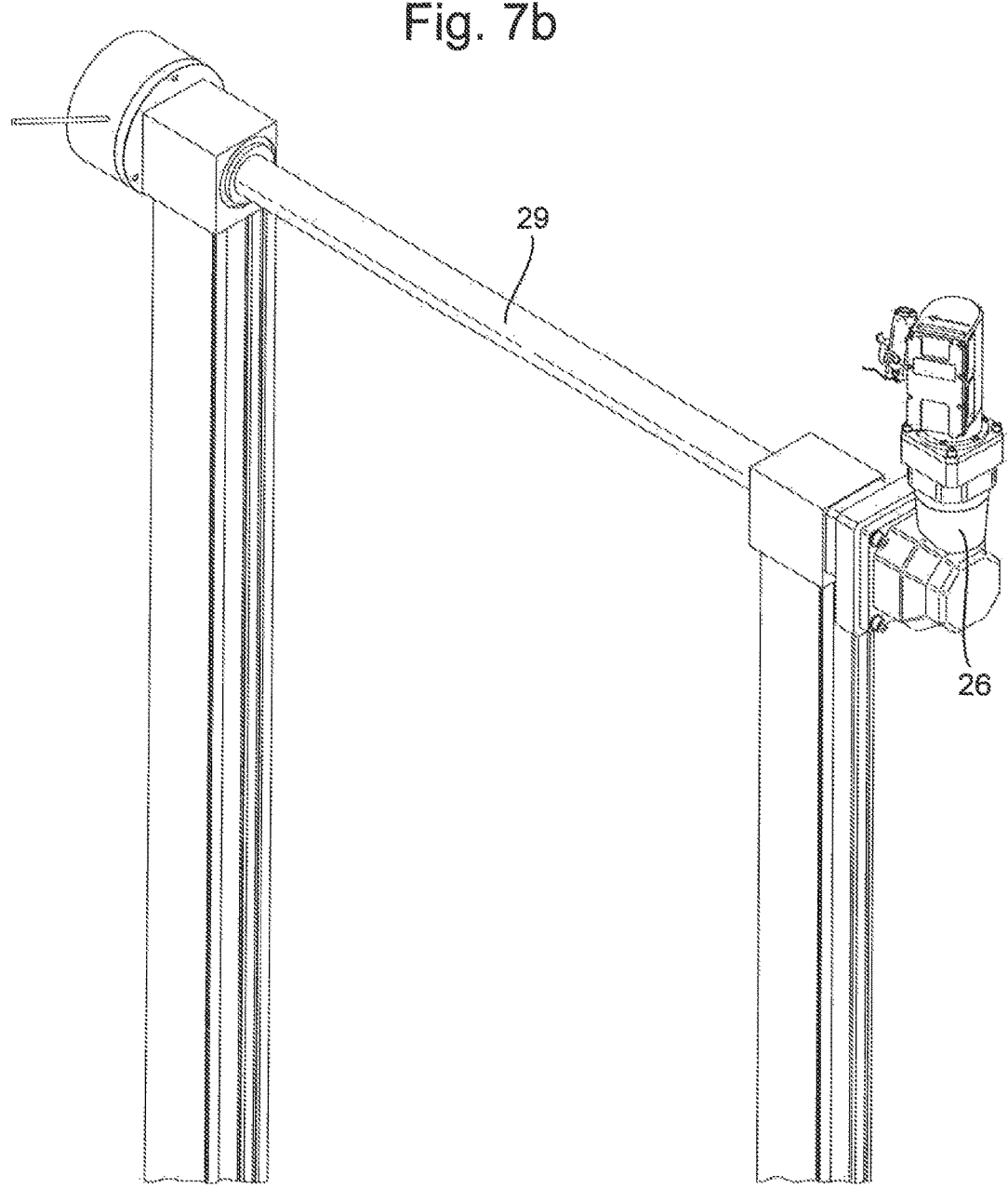

The first sub frame is provided with a first guide rail 24A which extends in a second direction $D_2$ wherein said second direction $D_2$ comprises a component in the vertical direction $D_v$ (see FIG. 7A). In this example $D_2$ extends in the vertical direction $D_v$. The first guide rail is for guiding, the radiation source if it is moved up or down in the second direction. The second sub frame 2B is provided with a second guide rail 24B which also extends in the second direction $D_2$. The second guide rail is for guiding the radiation detector up or down in the second direction. The radiation source 6 is moved up and down by means of a spindle or toothed belt which are driven by a second motor 26. The spindle or the belt are not shown in the drawing. If the radiation source is moved up by means of a spindle or toothed belt its movement is guided by means of the guiding rail 24A. Similarly the radiation detector 8 is moved up and down by means of a spindle or toothed belt which is not shown in the drawing. Also the spindle or toothed belt by which the radiation detector is moved up and down in the direction of $D_2$ is driven by the second motor 26. As can be clearly seen in FIG. 7B, the second motor 26 can easily drive the spindle or toothed belt which is attached to the radiation detector 8 because the motor 26 is in this example attached to the second guide rail 24B. The motor 26 also drives an axis 29 from which the length may be varied and which axis 29 extends between the first guide rail 24A and the second guide rail 24B. By means of the axis 29 the spindle or toothed belt which is attached to the radiation source 6 can be driven. Thus it holds that the radiation source is movable in the second direction and that it is movably attached to the first sub frame by means of the first guide rail. Furthermore the radiation detector is also movably attached to the second sub frame by means of the second guide rail 24B which is attached to the second sub frame. The system is provided with the second motor 26 for moving the radiation source and the radiation detector synchronically up and down in the second direction D2 for scanning a weld which extends in the second direction or particularly which extends in the vertical direction in this embodiment.

Figure 5:
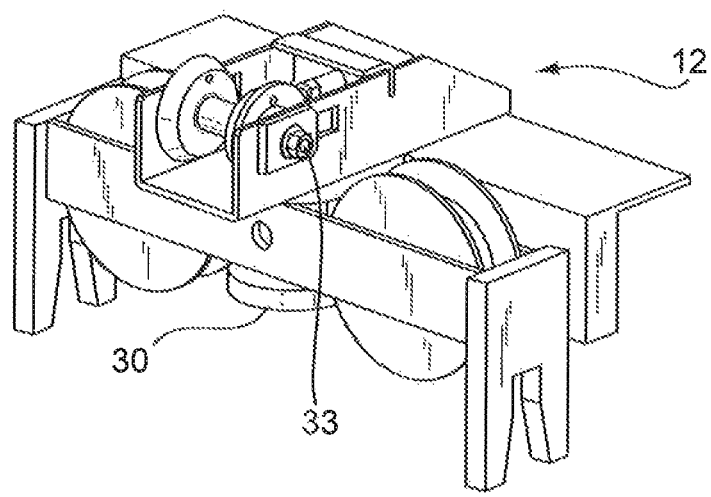
FIG. 5 shows a detail of the suspension transportation means as shown in FIG. 4.

Furthermore the system is provided with a damped suspension between the suspension wheels 14.1 to 14.4: as can be seen in FIG. 5 there is provided a rubber loaded hinged coupling block 30. The suspension transmission means are provided with a distance position slider 33 for varying a distance in a horizontal direction between the first sub frame and the second sub frame. This may be important to inspect walls with varying thickness. For the same reason the horizontal distance between the source and the first sub frame is adjustable as well as the horizontal distance between the radiation detector and the second sub frame is adjustable. As is furthermore shown in FIG. 2 the first sub frame is provided with at least one and in this embodiment four support wheels wherein a rotation axis of the first support wheels extends in a vertical direction. The first support wheels 32.1 to 32.4 are arranged to roll along the surface of the portion of the wall to be inspected if the system is moved over the upper edge. In this example also the second sub frame is provided with at least one support wheel and in this example with at least four support wheels 34.1 to 34.4 which are separated in a horizontal direction from each other wherein a rotational axis of each of the second support wheels extend in a vertical direction (in FIG. 14 *a* is shown that in fact 8 support wheels may be provided in pairs). The second support wheels are arranged to roll over a surface of a portion of the wall if the system is driven over the upper edge. The support wheels 32.1 to 32.4 and the support wheels 34.1 and 34.4 are provided for additional stability if this frame is moved in the direction of the upper edge while scanning a weld which extends in the direction of the upper edge. Also when scanning a weld which extends in vertical direction the support wheels are provided for additional stability while the system is stationary.

In this example the distance between at least one of the first support wheels and in this example between each of the four first support wheels on the one hand and the first sub frame on the other hand can be adjusted. Similarly the distance between at least one of the second support wheels and in this example each of the second support wheels on the one hand and the second sub frame on the other hand can be adjusted. In this example the distance between the support wheel and the first sub frame can be defined as the horizontal distance between said support wheel and the first sub frame. Similarly a distance between a second support wheel and the second sub frame can be defined as the horizontal distance between such support wheel and the second support sub frame.

The orientation of the rotational axis of the first and second support wheels may be changed such that the orientation of the rotational axis of these wheels becomes horizontal. In such a way the support wheels can roll along the outer surface of the wall during the installation of the first sub frame or second sub frame wherein the first and second sub frame are lowered while the support wheels are in contact with the outer surface of the wall to be inspected. The lowering will continue for example up until for the first sub frame it holds that the suspension wheels will contact the free upper edge of the wall to be inspected. For the second sub frame it holds that the second sub frame can for example be lowered wherein the support wheels roll along the outer surface of the wall in a vertically downward direction until the hooks 10 are attached to the already positioned first sub frame including the top portion of the sub frame.

In this example it holds that the radiation source is a line radiation source (actually, this means that it holds that the radiation source provides a radiation beam substantially shaped like a line) and that the radiation detector is a line radiation detector. The system is arranged so that the orientation of the radiation source for adjusting an angle φ1 between the line R of the radiation source (this line is the longitudinal direction of an opening of the source where through the radiation is transmitted) and the horizontal plane Q can be varied. More particularly, the line R can be chosen to extend perpendicularly to the upper edge of the wall for scanning welds which extend in the direction of the upper edge of the wall which direction is generally horizontal or in a horizontal direction for scanning welds which extend in a general vertical direction. Similarly the system is arranged to adjust the orientation of the radiation detector 8 for adjusting an angle φ2 between the line R2 of the radiation detector and a horizontal plane Q. (this line R2 is in this example the longitudinal direction of a surface of the detector which can receive radiation). As is explained for the radiation source it holds for the radiation detector that the line R2 in practice can be oriented perpendicular to the upper edge of the wall for scanning welds which extend in a direction of the upper edge of the wall which direction is generally a horizontal direction and wherein the line R2 can be directed in a horizontal direction for scanning welds which extend in a vertical direction.

In this example it holds that the radiation detector is a digital detector. In this example it further holds that the system is provided with a computer or controller 40 (see FIG. 3) communicatively connected to the digital detector for preferably instantaneously creating an image of the scan of the weld on the screen. In this example the radiation detector comprises a plurality of pixels wherein pixels 50 are arranged along a plurality of line segments 52 as shown in FIG. 10, wherein the line segments 52 extend parallel to each other. In other words the plurality of pixels are arranged in a rectangular pattern and divided over a two dimensional plane wherein the detector comprises a plurality of pixels separated in a longitudinal direction S (see FIG. 10) of the line detector (of the line R2) as well as a plurality of pixels separated in a direction T perpendicular to the longitudinal direction of the line. The latter line R 2 is defined as the direction of the line detector. The direction of R2 is the same as the direction S. The direction of the line segments 52 and the line R2 is also the same.

Furthermore it holds that the radiation source is an X-ray radiation source. Of course this means that the radiation detector should be able to detect X-rays.

As is shown in FIG. 7C the system is provided with a first radiation shield 56 for shielding the radiation source in all directions except for a direction L extending from the radiation source to the radiation detector. Furthermore the system is provided with a second radiation shield 60 for shielding the radiation detector preferably in all directions except for direction L from the radiation source to the radiation detector. Furthermore it holds that the system is provided with a third radiation shield which surrounds a path along which the radiation shield in use travels from the radiation source to the portion to the wall to be inspected and/or which surrounds a path along which the radiation shield in use travels from the portion of the wall towards the radiation detector. In FIG. 7C the third radiation shield comprises a first portion which is indicated with Ref. No. 58 and a second portion which can be the same as the shielding with Ref. No. 60 surrounding the detector.

The radiation source and/or in this example also the radiation detector are arranged to be retracted, for example for lifting the system or removing the system of a portion from the wall having welds to be inspected for this purpose. The system is provided with handles 61 and 63 for this feature.

In this example the mentioned motors, the radiation detector and the radiation source are each connected to the computer 40 to be controlled by the computer 40. In this example it further holds that there is a cable connection between a remote control unit 80 and the frame 2 for controlling the mechanical functions of the system such as controlling the motors for moving the frame to the next weld to be examined and for positioning the vertical positioning of the source and detector. The control unit 80 controls the functions which are used for moving the system in the direction of the upper edge 16 while scanning welds which extend in the direction of the upper edge and for moving the detector and the source synchronically up and down for detecting welds which extend in a vertical direction while the frame as such is stable and stationary relative to the upper edge of the wall in other words while the system is not driven by means of the motor 20.

The operation of the system described is as follows.

Figure 8A:
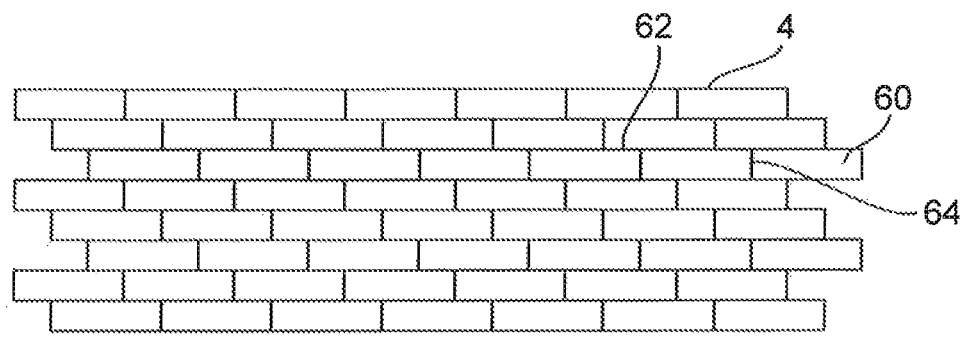
FIG. 8a shows a portion of a ring from a tank wall under construction.
Figure 8B:
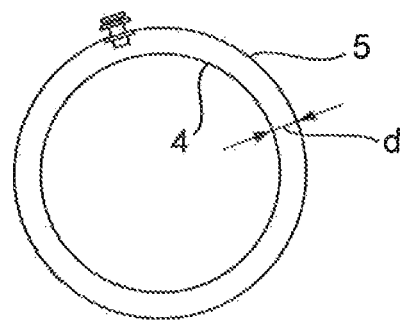
FIG. 8b shows a tank wall surrounded by a concrete wall.

FIG. 8A shows a finished tank wall 4 as viewed from an inside of the tank. The tank wall is erected from steel plates 60 in a brick like configuration. The steel plates may for example be 15 meters wide and 4 meters high. As shown in FIG. 8A the steel plates 60 are connected to each other by means of horizontal welds 62 and vertical welds 64. In some situations, like an LNG storage tank, often the tank wall 4 is surrounded by a concrete wall 5 as shown in FIG. 8B. In that case there is distance d between the wall metal wall 4 and the concrete wall 5. When the wall 4 is constructed a first step is that a plurality of plates are welded on a bottom plate 66 of the tank. As shown in FIG. 11A at a certain moment in time 5 plates 60 have been welded to the bottom plate 66 by means of a horizontal weld 68. Furthermore the plates 60 are connected to each other by means of vertical welds 64.$i$ ($i=1, 2, 3, \ldots$). Thus a portion of a first lower ring of the tank wall has been manufactured. This situation is also shown in FIG. 11 B by means of a solid line 4. In order to inspect the vertical welds 64.$i$ in a first step the first sub frame 2A together with the top portion 2C is lifted for example by means of a crane and positioned on the upper edge of the portion of the lower ring in such a way that the suspension wheels 14.1 to 14.4 are in contact with the upper edge 16.

In this way the first sub frame and the top portion are positioned on the first portion of the ring which has been manufactured. In the next step the second sub frame 2B is lifted up and positioned between the wall between the portion of the lower ring 70 which has been manufactured and the concrete wall 5. Then the second sub frame 2B is rigidly attached to the first sub frame 2A by means of the hooks 10. This is schematically shown in FIGS. 11A and 11B wherein the system 1 is positioned on top of the upper edge 16. The supported wheels 34.1 to 34.4 are adjusted in horizontal directions so that they are in contact with the outer surface 72 of the lower ring. Similarly the support wheels 32.1 and 32.4 are adjusted in horizontal directions so that they are in contact with the outer surface 73 of the lower ring laying opposite to the outer surface 72. Also the drive wheel 18 is positioned to be in contact with the outer surface 73. If required also the distance between the support wheels 14.1 to 14.4 and the second sub frame may be changed for a proper alignment of the system with the lower ring, depending on the thickness of the wall 4. Also the horizontal distance between the outer surface 72 and the radiation detector may be adjusted as well as the horizontal distance between the outer surface 73 and the radiation source 6 may be adjusted depending on the thickness of the wall.

Then subsequently by means of the remote control 80 the motor 20 is activated for moving the system over the upper edge 16 in the direction Q towards the vertical weld 64.2 as shown in FIG. 11A. The system is stopped as soon as the vertical plane V coincides with the vertical weld 64.2. It is made sure that the lines of the line source as well as the line detector are horizontally directed. Then by means of the computer 40 the motor 26 is activated for moving both the radiation source 6 and the radiation detector 8 in a synchronous way in a vertical direction for scanning the vertical weld 64.2. Because the radiation detector 8 is a digital detector, the measuring results are directly available and are submitted to the computer 40. The computer 40 generates an image of the scanned weld. It is remarked that it is also possible that the computer 40 merely submits the received information from the detector to a central computer, wherein the central computer processes the signals from the radiation detector for creating the image. Also the signals received from the digital detector may be stored in the computer 40 and/or the central computer for later verification. Thus the workers can immediately see whether or not the vertical weld meets the required standards. If the weld is not correct, it is possible to immediately notify the workers who are welding the next plates, so that they can inspect their process in order to solve any problem. This can be done after only a couple of plates have been welded together. Of course it is also possible that the weld meets the requirements.

Then by means of the remote control, the system 1 is moved further in the direction Q for example inspecting the weld 64.3 in the same manner as discussed in the same manner for the weld 64.2. Meanwhile the remainder of the first lower ring 70 is constructed by welding the plates together until a complete ring is constructed as shown by dotted lines in FIG. 11B. Each of the vertical welds of the complete lower ring are inspected in a way as discussed above.

It is noted that the horizontal weld 68 between the bottom plate 66 and the plates 60 of the lower ring are not inspected by means of the system but by means of other well known inspection system.

After the first ring 70 is finished, the workers start with a next ring 74 on top of the lower ring 70. In this case the plates of the next ring 74 are welded to the plates of the lower ring 70 by means of a horizontal weld 76. The plates of the ring 74 are welded together by means of vertical welds 64.1, 64.2 etc.

Figure 9:
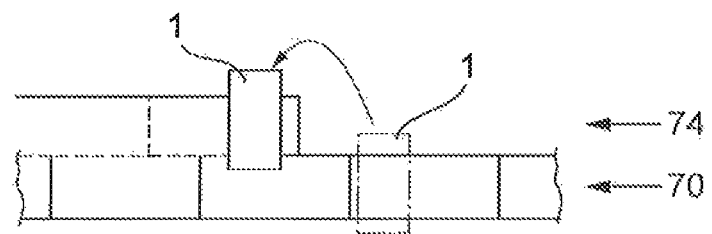
FIG. 9 shows that the system of FIG. 1 can be lifted from one (portion) of a ring to a next (portion) of a ring which is welded on top of a previously constructed portion of the ring.

By means of a crane the second sub frame 2B is disconnected from the first sub frame 2A. Then the first sub frame 2A is also lifted from the first ring 70. The first sub frame 2A are subsequently positioned on the upper edge formed by a portion of the next ring 74 which has meanwhile been constructed (FIG. 9). As can be seen in FIG. 12, the suspension wheels 14.1 to 14.4 are adjusted to a slightly higher position relative to the first sub frame 2A so that the frame 2 as a whole extends downwardly as a position below the horizontal weld 76. Also the hooks 10 of the second sub frame 2B are adjusted vertically and then the sub frame 2B is connected again to the first sub frame 2A so that it extends between the concrete wall 5 and the portion of the wall 4 which has meanwhile been constructed. This situation is shown in FIG. 12. It is also possible that the frame as a whole (without disconnecting the first sub frame and the second sub frame from each other; the frame is thus removed as a whole from the first ring 70) is moved by means of a crane from the first ring 70 on to the next ring 74.

Then for example in a first step, the motor 26 is activated by means of a remote control so as to position the radiation source 6 and the radiation detector 8 on the level of the horizontal weld 76. Furthermore each of the adjustments which have been made for the lower ring 70 may be repeated. Then the motor 18 is started for moving the system in the direction of the arrow Q meaning in the direction of the upper edge 16 of the next ring 74 for scanning the horizontal weld 76. After that the horizontal weld 76 is scanned; the vertical welds 64.1, 64.2 etc. can be inspected in a similar manner as discussed for the vertical weld 64.1, 64.2, 64.3 for the lower ring 70. Meanwhile during inspection the weld 76 and the vertical weld is finished as well as the vertical welds 64.1 to 64.5 the workers can continue finishing the complete next ring 74. The system will be used for scanning the remainder of the horizontal weld 76 as well as each of the new vertical welds 64.*i* from the next ring 74. Subsequently the workers may start with a next ring on top of the last ring 74 inspected wherein the whole process for inspecting this new ring 78 from the position is indicated in FIG. 12 in a similar way as discussed for the last inspected and constructed ring 74. All these steps are repeated until the complete wall 4 is constructed and each of the horizontal welds and vertical welds with the exception of the horizontal weld between the lower ring and the base plate are inspected by means of the system.

Thus it holds that the method discussed comprises the following steps:

1. Constructing at least a portion of a first lowest ring of the wall by welding metal plates to each other wherein the finished lowest ring comprises a plurality of metal plates which are connected to each other by vertically extending welds (and possibly horizontally extending weld as will be discussed later);
2. Installing the system so that the suspension means are positioned on an upper edge of the portion of the first ring of the tank wall which has been constructed in step 1;
3. Carrying out inspection of a vertical weld by moving the radiation source and the radiation detector synchronously in a vertical direction while keeping the frame stationary relative to the upper edge of the portion of the first ring;
4. Moving the system along the upper edge of the portion of the first ring to another position and repeat step 3.

5. Repeating step 4 until all vertical welds of the portion of the first ring have been scanned;
6. Optionally inspecting a horizontal weld between plates of the first ring by moving the system over the upper edge of the first ring;
7. Repeating step 1-6 until the first ring is fully constructed and each weld of the first ring is inspected;
8. Removing the system from the first ring of the tank wall and possibly adjusting the vertical position of the suspension wheels on the system;
9. Constructing at least a portion of a next ring on top of the last ring inspected wherein the plates of the next ring are connected to each other by vertical welds (and optionally horizontal welds as will be discussed later) and wherein plates of the next ring are attached to plates of the last ring by means of a horizontal weld;
10. Installing the system so that the suspension means are positioned on an upper edge of at least a portion of the next ring of the tank wall which has been constructed in step 9;
11. Carry out inspection of a vertical weld by moving the radiation source and the radiation detector synchronously in a vertical direction while keeping the frame stationary relative to the upper edge of the next ring;
12. Moving the system along the upper edge of the next ring to another position and repeat step 11.
13. Repeating step 12 until all vertical welds of the portion of the next ring have been scanned;
14. Moving the frame over the upper edge of the portion of the next ring for scanning the weld between the portion of the next ring and a last ring manufactured below the next ring and optionally for scanning the horizontal weld between the plates of the next ring;
15. Repeat steps 9-14 until the next ring is complete constructed and each vertical weld of the next ring is inspected, the complete horizontal weld between the next ring and the last ring as mentioned in step 9 also inspected and optionally the at least one horizontal weld between the plates of the next ring are inspected;
16. Removing the system from the next ring of the tank wall
17. Repeating steps 9-16 until the wall of the tank is finished and preferably each weld has been inspected.

The order of steps 11-14 can be varied and is not fixed, such as for example 11, 12, 13, 14 or 14, 11, 12, 13 or 11, 14, 12, 13.

It is also possible that a plurality of rings such as ring 70 and ring 74 are considered as a single ring to be inspected. For example if the height of two plates corresponds about or slightly is less than the height of the frame 2 rings 70 and 74 should be considered as subrings wherein subrings 70 and 74 together form a single ring as to be inspected first.

An Example is shown in FIG. 13 wherein rings 70 and 74 are in fact considered to be subrings from a ring having a height H which can be inspected by means of a system 1. In that case the system 1 will scan the horizontal weld 76 by positioning the radiation source and detector on the height of the horizontal weld 76. Furthermore each of the vertical welds 64 are scanned in a similar way as discussed in relation to FIGS. 11A and 12. Once the complete ring 70,74 is inspected a next ring 78 can be welded on the lower ring 70, 74 by means of a horizontal weld 84. In that case it may be that the frame 2 is positioned on the upper edge 16 of the next ring 78 for inspecting the weld 84 and the vertical welds between the plates of the next ring 78 (in FIG. 13 the frame is in that case shown in dotted lines and is also indicated with 2').

It is however also possible that a ring 78 as well as a ring 82 are constructed and that only after the ring 78 and at least a portion of the ring 82 or the complete ring 82 is constructed the system is positioned on the upper edge of the ring 82 for inspecting the welds of the ring 78 and the ring 82. In that case the rings 78 and 82 are considered in combination as a new ring to be inspected which new of next ring not only comprise vertical weld but also a horizontal weld (the frame is in that case shown in FIG. 13 with dotted lines and is also indicated with 2").

Thus a ring can be regarded as a collection of plates which are ordered relative to each other on the same horizontal level. A ring can however also be considered as a collection of plates which are ordered relative to each other in a varying horizontal and vertical direction such as a combination of the (sub) rings 70, 74 as shown in FIG. 13 or even a combination of rings 70,74 and 76 or a combination of rings 76 and 82.

Thus in that case a method for constructing a vertical wall comprises the following steps:

1. Constructing at least a portion of a first lowest ring of the wall by welding metal plates to each other wherein the finished lowest ring comprises a plurality of metal plates which are connected to each other by vertically extending welds and horizontally extending weld;
2. Installing the system so that the suspension means are positioned on an upper edge of the portion of the first ring of the tank wall which has been constructed in step 1;
3. Carrying out inspection of a vertical weld by moving the radiation source and the radiation detector synchronously in a vertical direction while keeping the frame stationary relative to the upper edge of the portion of the first ring;
4. Moving the system along the upper edge of the portion of the first ring to another position and repeat step 3.
5. Repeating step 4 until all vertical welds of the portion of the first ring have been scanned;
6. Inspecting a horizontal weld between plates of the first ring by moving the system over the upper edge of the first ring;
7. Repeating step 1-6 until the first ring is fully constructed and each weld of the first ring is inspected;
8. Removing the system from the first ring of the tank wall and optionally adjusting the vertical position of the suspension means relative to the frame of the system;
9. Constructing at least a portion of a next ring on top of the last ring inspected wherein the plates of the next ring are connected to each other by vertical welds and horizontal welds and wherein plates of the next ring are attached to plates of the last ring by means of a horizontal weld;
10. Installing the system so that the suspension means are positioned on an upper edge of at least a portion of the next ring of the tank wall which has been constructed in step 9;
11. Carry out inspection of a vertical weld by moving the radiation source and the radiation detector synchronously in a vertical direction while keeping the frame stationary relative to the upper edge of the next ring;
12. Moving the system along the upper edge of the next ring to another position and repeat step 11.
13. Repeating step 12 until all vertical welds of the portion of the next ring have been scanned;
14. Moving the frame over the upper edge of the portion of the next ring for scanning the weld between the portion of the next ring and a last ring manufactured below the next ring and for scanning the horizontal weld between the plates of the next ring;
15. Repeat steps 9-14 until the next ring is complete constructed and each vertical weld of the next ring is inspected, the complete horizontal weld between the next ring and the last ring as mentioned in step 9 also inspected and the at least one horizontal weld between the plates of the next ring are inspected;
16. Removing the system from the next ring of the tank wall
17. Repeating steps 9-16 until the wall of the tank is finished and preferably each weld has been inspected.

It is noted that other methods are also possible, for example it is possible to start inspecting a ring such as ring 74 only after that it has been completely finalized. In that case the method comprises the following steps:

1. Constructing a first lowest ring of the wall by welding metal plates to each other wherein the finished lowest ring comprises a plurality of metal plates which are connected to each other by vertically extending welds;
2. Installing the system so that the suspension means are positioned on an upper edge of at least a portion of the first ring of the tank wall which has been constructed in step 1;
3. Carrying out inspection of vertical welds by moving the radiation source and the radiation detector synchronously in a vertical direction while keeping the frame stationary relative to the upper edge of the first ring;
4. Moving the system along the upper edge of the portion of the first ring to another position and repeat step 3.
5. Repeating step 4 until all vertical welds have been scanned;
6. Removing the system from the first ring of the tank wall and optionally adjusting the vertical position of the suspension wheels on the system;
7. Constructing a next ring on top of the last ring inspected wherein the plates of the next ring are welded to each other by means of vertical welds and wherein the plates of the next ring are welded to the last ring by means of a preferably horizontal extending weld.
8. Installing the system so that the suspension means are positioned on an upper edge of at least a portion of the next ring of the tank wall which has been constructed in step 7;
9. Carry out inspection of vertical welds by moving the radiation source and the radiation detector synchronously in a vertical direction while keeping the frame stationary relative to the upper edge of the next ring;
10. Moving the system along the upper edge of the next ring to another position and repeat step 9.
11. Repeating step 10 until all vertical welds of the next ring have been scanned;
12. Moving the frame over the upper edge of the portion of the next ring for scanning the weld between the portion of the next ring and a ring below the next ring
13. Removing the system from the next ring of the tank wall
14. Repeating steps 7-13 until the wall of the tank is finished and preferably each weld has been inspected.

The method and the system according to the invention is not limited to the present embodiment. For example, the support wheels 34.1 to 34.4 on the second frame may be replaced by 8 support wheels as is shown in FIG. 14A and FIG. 14B. As is shown in FIG. 14A the second sub frame comprises two first support wheels 90.1 and 90.2 which are separated in at least a vertical direction from each other. Furthermore the first sub frame comprises two support wheels 90.1 and 90.4 which are also separated in at least a vertical direction from each other. The arrangement of the support wheels 90.1-90.4 is shown in more detail in FIG. 14b. Similarly other support wheels 92.1 to 92.24 are provided. Again each of the support wheels are arranged to roll along the surface of the portion of the wall if the system is moved over the upper edge of the wall. The support wheels 90.1 and 90.2 are located on the second sub frame in a vertical direction in such a way that the support wheel 90.1 lays below a horizontal weld to be inspected whereas the support wheel 90.2 lays above the same horizontal weld to be inspected. The same applies to support wheels 90.3 and 90.4 respectively. Also the same applies to the support wheels 92.1 and 92.2 respectively as well as to support wheels 92.3 and 92.4 respectively. The support wheels 90.1 and 90.2 can be adjusted in a horizontal direction in such a way that the support wheel 90.1 is in contact with or lays free from the wall below a horizontal weld to be inspected whereas the support wheel 90.2 is in contact with or lays free from the wall above the same horizontal weld to be inspected. When during horizontal scanning the system passes a vertical weld the associated support wheels above or below the horizontal weld can be moved away from the wall surface to avoid any mechanical influences due to surface irregularities like a weld cap (weld reinforcement). Again this provides an additional stability to the system. In this example the top portion 2C is rigidly integrated with the first sub frame 2A. However, it is also possible that the top portion 2C is rigidly integrated with the second sub frame 2B. Also in this example one radiation source 6 and one radiation detector 8 are provided. It is however also possible that the plurality of radiation sources as well as a plurality of radiation detectors are provided. Such varieties all fall within the scope of the present application. Important features of the present invention which may but need not be implied in an embodiment of the invention are amongst others that:

The inspection system follows the welding process at a certain distance, moving around the ring. In the same way the horizontal weld is inspected, a certain distance following the welding process for the horizontal weld. Once the examination all the vertical welds and the horizontal weld of a ring is finished and the placement of plates for the next ring is in process, the scanner system will be lifted onto the next ring before that next ring is closed, as shown FIG. 9.

Scaffolding is placed on the inside of the tank wall to provide access to the ring under construction. The scaffolding is mounted (up-) to the highest ring of plates that is completely welded, just below the ring under construction.

As shown in FIG. 1 the system is positioned over the vertical plates of the storage tank shell (wall) like an inverted U, with the X-ray source on one side (inside the tank) and the detector on the other side (outside the tank).

The system consists of 2 sides that are combined and lifted as one part onto the tank plates:

X-Ray source frame (also referred to a first sub frame)
Detector frame (also referred to as second sub frame)

The basic concept is that the source frame can be installed as a first component onto the tank wall, at the inside of the tank wall, hanging on its carriage wheels. The X-Ray source frame carries all the heavy X-Ray equipment. Then the detector frame is lifted to the outside of the tank wall and hooked onto the source frame with two hinge like connections with a tight fit, to avoid independent horizontal movement of the two frames. Together the source frame and detector frame form the basis of the system. Alternatively, the source frame can be installed on a separate vertical plate or assembly, hanging on its carriage wheels. Then the detector frame is lifted and hooked onto the source frame, so the complete system can be lifted onto the tank wall. The detector frame has no support wheels but is suspended from the source frame, allowing the lower parts of the source frame and of the detector frame to move some distance perpendicular to the tank wall independently while no movement is possible parallel to the tank wall due to the rigid connection in that direction.

At the end of the project the detector frame can first be separated from the source frame to uninstall the system.

The main components of both frames are vertical legs that hold the vertical guiding arrangement and platforms to place the equipment. Ladders are integrated in the scanner frames to be able to climb up/down from/to the platform on top of the scanner. The scanner can be accessed from the scaffolding on the source side, the detector side can be accessed via the top platform and using the integrated ladders.

From perspective of inspection quality and X-Ray safety, the movement of the radiation source (including shielding) and radiation detector (including shielding) on either side of the plate is mechanically coupled.

Two separate drive units are present, one for horizontal scanning and one for vertical scanning respectively.

For some tank plate materials it is important that each components of the system that could become into contact with the tank wall should be selected to avoid contamination, especially in the weld areas and on the weld preparation at the top of the plate sections.

Vibrations and shocks to the system can impact the image quality, especially if these lead to displacements of the detector in X and Y direction (plane parallel to tank wall). Therefore measures have to be taken to avoid impact.

Vibrations and shocks can be induced to the scanner system in several manners:

From wheels rolling on irregular surface
Accelerations and decelerations of system
Moving components inside the scanner (motor vibrations, guidings)
External obstructions (cables dragging along wall or scaffolding)
Vibrations of the tank wall The low scanning speed and high mass of the system make that vibrations through the wheels can easily be suppressed with proper suspensions on the wheels.

Accelerations and decelerations to the system can induce swing or shocks in the system that can induce system vibrations (Eigen frequencies). This was solved with proper stiffness of the construction and removing potential sources. One possible source is from passing welds with support wheels. Either wheels should avoid these or weld caps should be grinded. Another source is acceleration from the motors, this can be tuned to avoid system vibrations. Also tuning the speed of the system can be used to avoid inducing vibrations.

With correct use of motors, gears and guiding methods, vibrations from moving components in the scanner can be avoided.

For induced vibrations and shocks from external obstructions, this is similar to induced swing and shock from accelerations or decelerations. Take special care for cable management to avoid for instance cables can get entrapped at the scaffolding, support points etc.

Vibrations of the tank wall cause movements perpendicular to the tank wall and if excessive can induce bouncing of the system or detector towards the wall. This can be difficult to solve. However with regard to the foreseen tank projects impact from tank wall vibrations is not expected.

Figure 2:
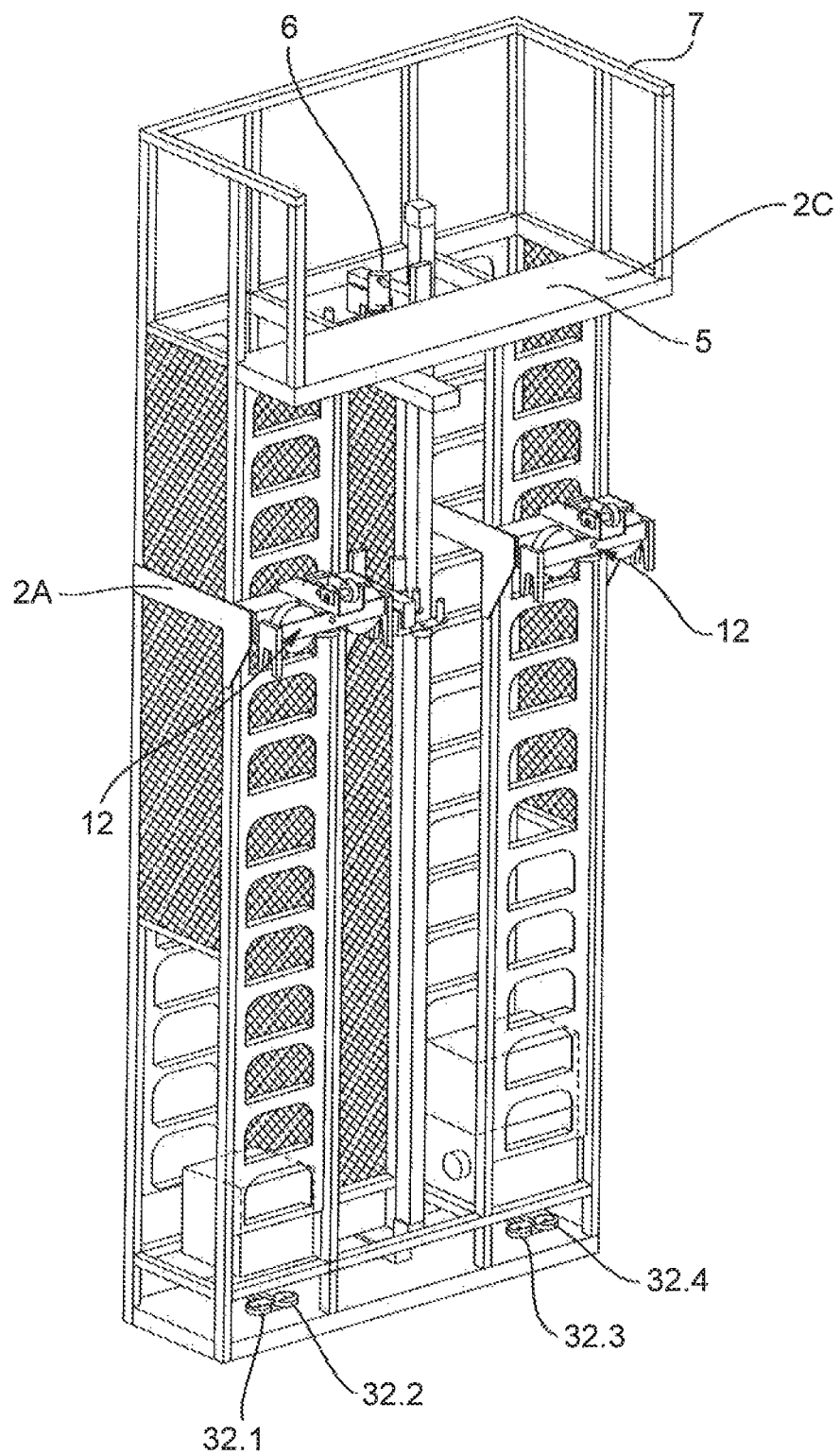
FIG. 2 shows a first sub frame and upper portion of the frame wherein the first sub frame is provided with a radiation source.

As shown in FIG. 2 the first sub frame consists of a rigid aluminum frame in which the X-Ray equipment is placed. The side of the first sub frame facing the tank wall has an open "window" to be able to scan the vertical welds over the full height without obstacles of the first sub frame.

Figure 3:
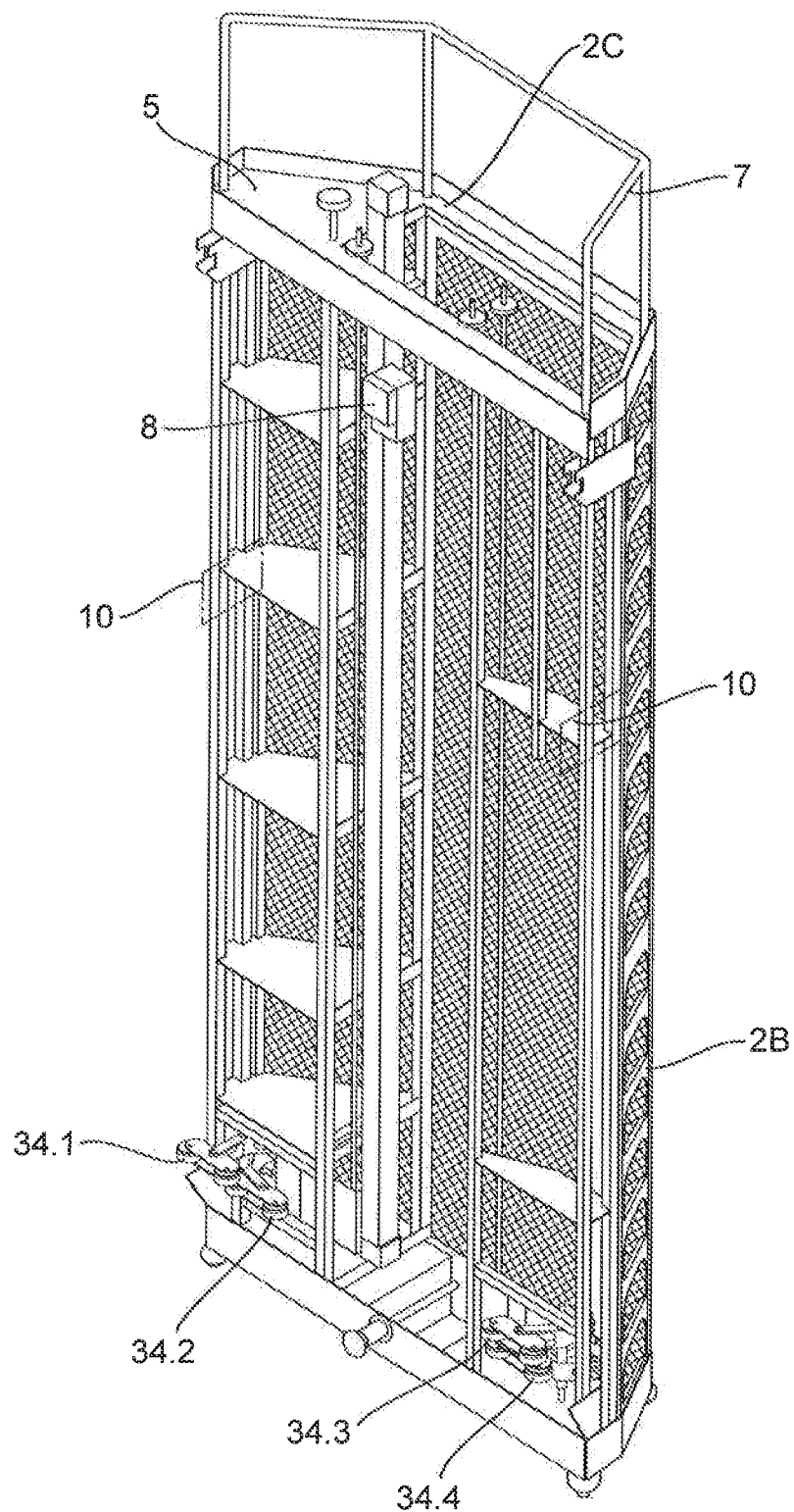
FIG. 3 shows a second sub frame provided with a radiation detector.

As shown in FIG. 3 the second sub frame is smaller than the first sub frame to fit in the limited space between the tank wall and concrete wall that is typically present at LNG tanks. Only the minimum required equipment is carried by the second sub frame, being the detector itself and an electronic junction box.

Figure 6:
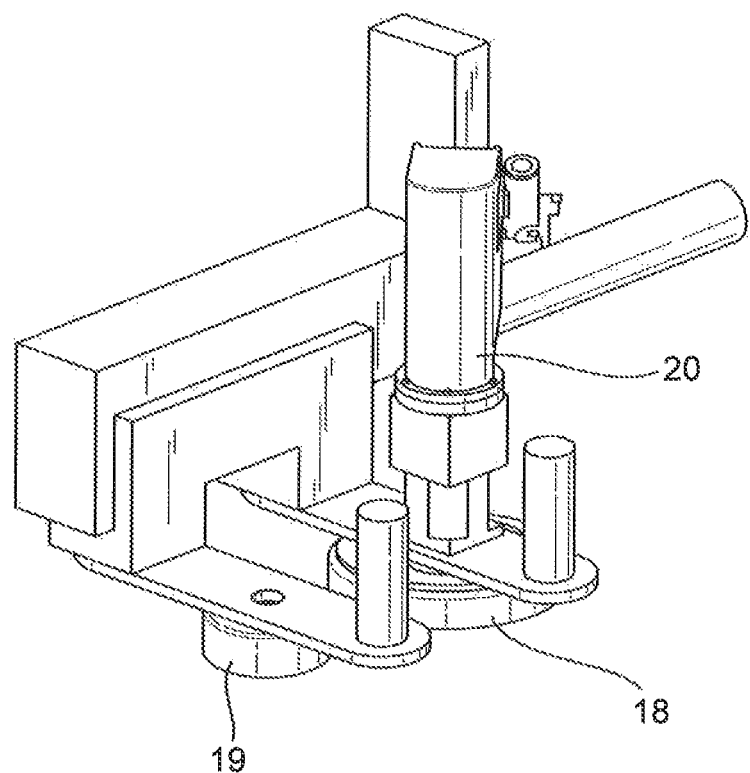
FIG. 6 shows an element of the movement means of FIG. 2.

As shown in FIG. 2 sets of carriage wheels together with the horizontal drive unit are mounted to the first sub frame with heavy support plates. The carriages can be mounted to the support frame at various heights to adapt the scanner to specific plate sizes As shown in FIG. 4 the top carriages have the following features:
- Double flanged wheels are used to assure that the scanner cannot drive off from the tank wall.
- Each wheel set consist of 2 wheels mounted in a frame that is mounted to the suspension with a rubber loaded hinged block. The rubber loading allows limited rotational freedom in 2 directions and absorbs vibrations coming from the wheels
- In order to align and set the distance with respect to the tank wall the mounting bars are mounted on a slider block to allow adjustment of the second frame to wall distance when installed on the tank wall
- Mounting bars for the detector frame. The detector frame can be hooked onto the mounting bars and secured to connect both frames As shown in FIG. 6 for the horizontal scanning a drive unit is placed at the top of the tank wall and moves the complete system. The frames have a high stiffness to achieve stability and accuracy for the horizontal movement.

The horizontal drive unit has the following features:
- A motor and gearing
- A traction wheel with PU surface for traction
- A support wheel on the outer side of the tank wall and spring loading between traction wheel and support wheel to apply a high pressure force to the wall
- For installation, the driving unit can be rotated upward to ride off from the tank wall As shown in FIG. 7b for the vertical scanning the system is equipped with guiding systems consisting of a guiding frame and timing belt. Each belt is connected to a sledge on the vertical guide rails. On this sledge the source or detector can be mounted. Alternatively, for the vertical movement spindles could be used.

The belt drives between both sides are mechanically coupled with an axle which may have an adjustable length and/or a universal joint. In this manner both vertical movements can driven with a single motor.

The source head and detector are positioned in the center of the system, in the center between the carriage wheels (in horizontal direction) for optimal mechanical protection and for alignment with the tank wall.

Figure 7D:
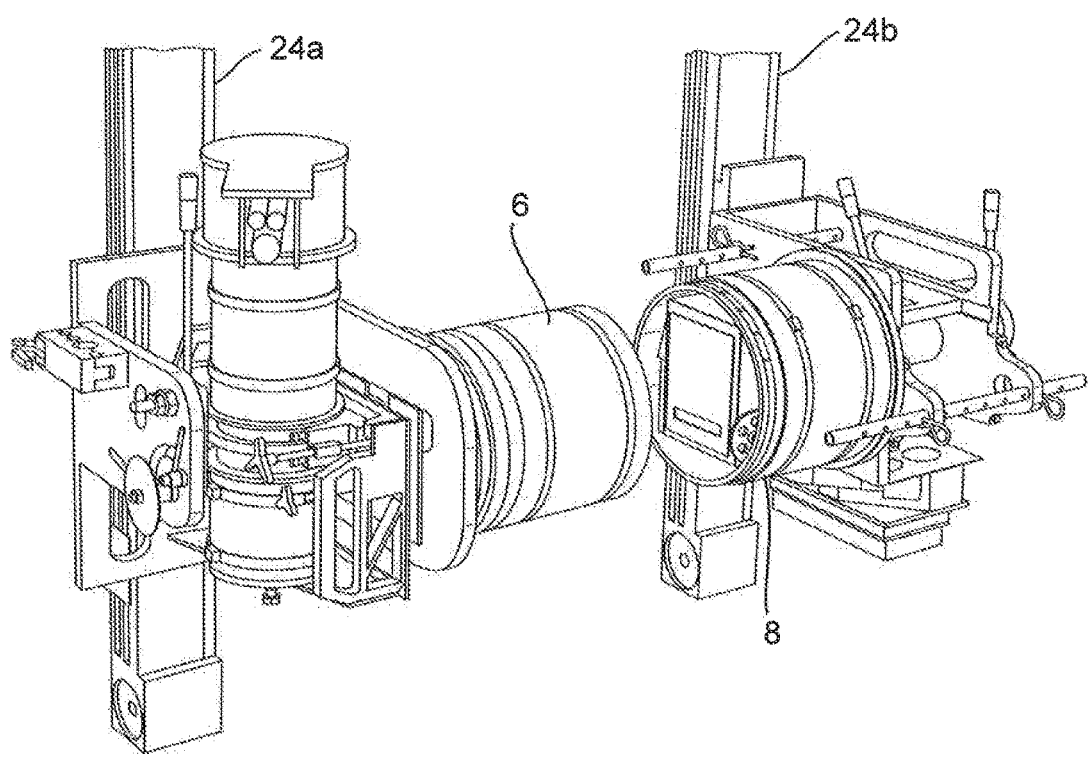
FIG. 7d shows a detail as shown in FIG. 7 from a different point of view indicated with the arrow p in FIG. 7c.

As shown in FIGS. 7C and 7D the X-Ray source and detector are mounted on the sledges of the vertical guiding rails by specially designed suspensions having the specific features.

Features radiation source:
- Adjustments tilt angle, rotational angle, height of source
- Rotation mechanism vertical-horizontal weld inspection
- Adjustable shielding towards tank wall Features detector unit:
- Mechanism to position detector towards tank wall
- Wheels on detector to follow tank wall contour
- Spring loaded suspension for detector
- Rotation mechanism vertical-horizontal weld inspection
- Detector unit can be rotated down to protect detector when lifting the system The radiation detector must be large enough to cover the width of the weld and also a part of the plate material, including the heat affected zone next to the weld. The radiation detector converts the radiation energy into an electrical signal, directly or indirectly. Individual exposures (frames) are measured at short time intervals, for example, 300 frames per second. For dynamic examination (scanning) the radiation detector is preferably a line detector, meaning that only a single line of pixels is measured to avoid unsharp results due to movement of the radiation source and detector relative to the object under examination during each frame. Alternatively an array detector can be used that has multiple pixels in the direction of movement, provided that the measured data is corrected for the different positions and movement. Such a correction can be time delayed integration as known technology. Such a detector can have, for example, 2200×60 pixels of 100×100 micrometer each. In this example the 60 pixels are substantially aligned with the scanning direction.

The system generates X-Rays during operation hence for a safe operation it is required to keep an exclusion zone. When the system is active, generating X-Rays, any person must be outside this exclusion zone, also the radiography operators. To limit the size of the exclusion zone the radiation source and detector are entirely enclosed with a protective (lead, tungsten) shielding to reduce emission of X-Rays in the surrounding area of the system. Obviously, no shielding is present between the radiation source, the plate and the radiation detector. In addition the radiation beam is collimated (restricted) to only the active part of the detector. The shielding is designed to take the direct beam and scattered radiation on the tank wall into account. Due to this dedicated shielding the exclusion zone is reduced to 3 meters around the contours of the system. This is much smaller compared to conventional radiography where typically no shielding is used and the exclusion zone can extend over part or even the complete tank.

The source and detector are fragile and expensive components. Therefore the system is designed to avoid accidental impact:
- Collisions during installation/hoisting
- Free fall of detector suspension (in case of vertical guiding/scanning) due to electrical or mechanical malfunction (brake in FIG. 7B)

The system is provided with mechanical means to rotate the radiation source and radiation detector 90 degrees to switch over from scanning horizontal welds to vertical weld and vice versa. This is required when, for example, the detector is a line detector and the radiation beam is collimated (restricted) to only the active area of such detector. When rotating, the detector and source should be kept aligned. However, it is not necessary (and with respect to mass center not beneficial) to rotate through the centreline of the X-Ray beam.

These features may but need not be applied in combination without leaving from the spirit of the invention as defined in the attached claims.

The invention claimed is:

1. A system for radiographic inspection of welds from at least a portion of a vertical wall wherein the wall comprising a plurality of metal plates connected by means of the welds, the system comprising
    a frame comprising a first sub frame positioned on a first side of the at least a portion of the vertical wall and a second sub frame positioned on a second side of the at least a portion of the vertical wall which lays opposite to the first side of the at least a portion of the vertical wall and wherein each of the sub frames extend downwardly from a top portion of the frame;

a radiation source which is attached to the first sub frame for transmitting electromagnetic radiation towards the weld and a radiation detector which is attached to the second sub frame for detecting radiation which has traveled through the weld or plate for carrying out the inspection, wherein the system is arranged such that the first sub frame and the second sub frame are mechanically connected to each other;

suspension transportation means connected to an upper portion of the frame wherein the suspension transportation means are positioned on an upper free edge of the at least a portion of the vertical wall so that the frame can drive over the upper free edge of the at least a portion of the vertical wall for scanning a weld to be inspected by means of the radiation source and the radiation detector wherein the weld extends in a direction of the upper edge of the at least a portion of the vertical wall;

wherein the first sub frame has a longitudinal shape extending in a vertical direction and/or wherein the second sub frame has a longitudinal shape extending in a vertical direction;

wherein the first sub frame and the second sub frame are connected to each other;

wherein the system is provided with at least a first motor for driving movement means which are in contact with an outer surface of the at least a portion of the vertical wall for scanning a weld which extends along the direction of the upper edge of the at least a portion of the vertical wall;

wherein the system is arranged to perform the scanning in the direction of the upper edge by moving the complete system;

wherein the radiation source and the radiation detector are aligned to each other, such that radiation which is transmitted by the radiation source could directly travel to the radiation detector along a straight line if there would not be a portion of the wall between the radiation source and the radiation detector;

wherein the radiation source is movably, in a second direction comprising a vertical component, attached to the first sub frame wherein the radiation detector is movably, in the second direction, attached to the second sub frame; and wherein the position of the radiation detector is adjustable in a direction towards and away from the first sub frame.

2. The system according to claim 1, wherein the first sub frame and the second sub frame are arranged to be disconnected from each other for removing the system from the wall.

3. The system according to claim 1, wherein the top portion is formed by an upper part of the first sub frame and an upper part of the second sub frame.

4. The system according to claim 1, wherein the system is provided with at least one further wheel which is arranged to roll along a surface of the wall opposite to the outer surface of the wall which is in contact with the movement means.

5. The system according to claim 4, wherein the system is arranged to perform the scanning in the direction of the upper edge by moving the complete system at a substantially constant speed.

6. The system according to claim 1, wherein the system comprises a plurality of suspension wheels which are separated from each other in a horizontal direction.

7. The system according to claim 6, wherein the radiation source and the radiation detector lay in a vertical plane wherein at least one of the suspension wheels lays on a first side of the vertical plane an at least another of the suspension wheels lays on an other side of the vertical plane.

8. The system according to claim 1, wherein the system is provided with a second motor for moving the radiation source and radiation detector synchronously for scanning a weld which extend in the second direction.

9. The system according to claim 8, wherein, the radiation source and the radiation detector are each moved by means of a spindle or toothed belt driven by the second motor.

10. The system according to claim 8, wherein the first sub frame is provided with a first guiderail extending in the second direction for guiding the radiation source when it is moved in the second direction by means of the second motor and wherein the second sub frame is provided with a second guiderail extending in the second direction for guiding the radiation detector when it is moved by means of the second motor.

11. The system according to claim 8, wherein the system is arranged to perform a scan in the second direction while the suspension transportation means are stationary and/or in that during the vertical scanning the alignment between radiation source and detector is maintained.

12. The system according to claim 1, wherein the system is provided with a damped suspension between the suspension transportation means on the one hand and the frame on the other hand.

13. The system according to claim 1, wherein the first sub frame is provided with at least one first support wheel wherein a rotational axis of the first support wheels extends in a vertical direction and wherein the first support wheel is arranged to roll along a surface of the at least a portion of the vertical wall and/or wherein the second sub frame is provided with at least one second support wheel wherein a rotational axis of the second support wheels extends in a vertical direction and wherein the second support wheel is arranged to roll along a surface of the at least a portion of the vertical wall if the system is driven over the upper edge.

14. The system according to claim 13, wherein the first sub frame is provided with at least two first support wheels which are separated in at least a vertical direction from each other and wherein a rotational axis of the first support wheels extends in a vertical direction and wherein the first support wheels are arranged to roll along a surface of the at least a portion of the vertical wall and/or wherein the second sub frame is provided with at least two second support wheels which are separated in at least a vertical direction from each other and wherein a rotational axis of the second support wheels extends in a vertical direction and wherein the second support wheels are arranged to roll along a surface of the at least a portion of the vertical wall.

15. The system according to claim 14, wherein the first support wheels can be adjusted in a vertical direction in order to position one of the first support wheels above a weld to be inspected and which extend in the direction of the upper edge and another one of the first support wheels below the weld to be inspected and/or in that the second support wheels can be adjusted in a vertical direction in order to position one of the second support wheels above a weld to be inspected and which extend in the direction of the upper edge and another one of the second support wheels below the weld to be inspected.

16. The system according to claim 13, wherein the distance between at least one first support wheel and the first sub frame can be adjusted in order to position the at least one first support wheel into contact with the wall or to position the at least one first support wheel free form the wall and/or that a distance between at least one second support wheel and the second frame can be adjusted in order to position the at least one second support wheel into contact with the wall or to position the at least one second support wheel free form the wall.

17. The system according to claim 13, wherein the system is arranged to orientate the rotational axis of the at least one first support wheel in a horizontal direction and/or wherein that the system is arranged to orientate the rotational axis of the at least one second support wheel in a horizontal direction.

18. The system according to claim 1, wherein, the position of the radiation source is adjustable in a direction towards and away from the second sub frame.

19. The system according to claim 1, wherein the position of the suspension transmission means is adjustable in a horizontal direction towards and away from the first sub frame and/or that the position of the suspension transmissions means relative to the frame is adjustable in a vertical direction.

20. The system according to claim 1, wherein the radiation source is a line radiation source and/or in that the radiation detector is a line radiation detector.

21. The system according to claim 20, wherein the system is arranged to adjust an orientation of the radiation source for adjusting an angle between the line of the radiation source and a horizontal plane and/or in that the system is arranged to adjust an orientation of the radiation detector for adjusting an angle between the line of the radiation detector and a horizontal plane.

22. The system according to claim 1, wherein the radiation detector is a digital detector.

23. The system according to claim 22, wherein the system is provided with a computer connected to the digital connector for instantaneously creating an image of the scanned weld on a screen.

24. The system according to claim 20, wherein the radiation detector comprises a plurality of pixels wherein the pixels are arranged along a pluralities of lines wherein said lines extend parallel to each other; or wherein the plurality of pixels are arranged in a regular pattern and divided over two dimensional plane wherein the detector comprises a plurality of pixels separated in the longitudinal direction of the line as well as a plurality of pixels separated in a direction perpendicular to the longitudinal direction of the line.

25. The system according to claim 1, wherein the radiation source is an X-ray radiation source.

26. The system according to claim 25, wherein the system is provided with a first radiation shield for shielding the radiation source in all directions accept for a direction from the radiation source towards the radiation detector.

27. The system according to claim 25, wherein the system is provided with a second radiation shield for shielding the radiation detector in all directions accept for a direction from the radiation source towards the radiation detector.

28. The system according to claim 25, wherein the system is provided with a third radiation shield which surrounds a path along which the radiation travels from the radiation source to portion of the wall and/or from the at least a portion of the vertical wall towards the radiation detector.

29. The system according to claim 26, wherein at least one of the radiation shields is arranged to be retracted for lifting the system or removing the system from the portion of the wall having welds to be inspected.

30. The system according to claim 1, wherein radiation source and/or the radiation detector are arranged to be retracted for lifting the system or removing the system from the portion of the wall having welds to be inspected.

31. The system according to claim 1, wherein the system is arranged to be remote controlled.

32. The system according to claim 1 wherein the upper edge of the at least a portion of the vertical wall extends in a horizontal direction.

33. The system according to claim 8, wherein the second direction is a vertical direction.

* * * * *